(12) United States Patent
Bolmsjö et al.

(10) Patent No.: US 8,475,435 B2
(45) Date of Patent: Jul. 2, 2013

(54) PARTIAL-LENGTH INDWELLING URINARY CATHETER PERMITTING SELECTIVE URINE DISCHARGE

(75) Inventors: Magnus Bolmsjö, Lund (SE); Sonny Schelin, Rockneby (SE); Per Andersson, Helsingborg (SE); Stephan Dymling, Limhamn (SE)

(73) Assignee: ProstaLund AB, Lund (SE)

( * ) Notice: Subject to any disclaimer, the term of this patent is extended or adjusted under 35 U.S.C. 154(b) by 686 days.

(21) Appl. No.: 12/648,087

(22) Filed: Dec. 28, 2009

(65) Prior Publication Data

US 2010/0106142 A1     Apr. 29, 2010

Related U.S. Application Data

(60) Division of application No. 11/246,801, filed on Oct. 7, 2005, now Pat. No. 7,662,145, which is a continuation-in-part of application No. 10/665,742, filed on Sep. 17, 2003, now Pat. No. 7,766,899.

(51) Int. Cl.
| | |
|---|---|
| *A61M 27/00* | (2006.01) |
| *A61M 1/00* | (2006.01) |
| *A61M 29/00* | (2006.01) |
| *A61M 29/02* | (2006.01) |
| *A61M 25/00* | (2006.01) |
| *A61M 25/10* | (2006.01) |
| *A61F 2/04* | (2006.01) |

(52) U.S. Cl.
USPC ............ 604/544; 604/540; 604/8; 604/96.01; 604/97.01; 604/99.01; 623/11.11; 623/23.64

(58) Field of Classification Search
USPC .................. 604/544, 540, 8, 9, 10, 48, 96.01, 604/97.01, 99.01; 623/11.11, 23.64
See application file for complete search history.

(56) References Cited

U.S. PATENT DOCUMENTS

| | | | | |
|---|---|---|---|---|
| 5,466,222 | A * | 11/1995 | Ressemann et al. | 604/103.09 |
| 5,569,219 | A * | 10/1996 | Hakki et al. | 604/524 |
| 6,494,855 | B2 * | 12/2002 | Rioux et al. | 602/67 |
| 7,662,145 | B2 * | 2/2010 | Bolmsjo et al. | 604/544 |
| 7,766,899 | B2 * | 8/2010 | Bolmsjo et al. | 604/540 |
| 2002/0032486 | A1 * | 3/2002 | Lazarovitz et al. | 623/23.67 |
| 2002/0072788 | A1 * | 6/2002 | Hammond et al. | 623/1.11 |
| 2002/0151923 | A1 * | 10/2002 | Holzer | 606/193 |
| 2003/0078467 | A1 * | 4/2003 | Whalen et al. | 600/30 |

* cited by examiner

*Primary Examiner* — Adam Marcetich
(74) *Attorney, Agent, or Firm* — John R. Ley

(57) ABSTRACT

A partial-length catheter, or an extendable tube or sleeve member of the catheter, is selectively movable within the prostatic urethra to open a urine drainage passageway through and obstructed portion of the prostatic urethra or to open the external urinary sphincter muscle and thereby discharge urine from the bladder. A control element is manipulated at a position exterior of the urinary canal to selectively move the catheter or the extendable tube or sleeve member, thereby selectively controlling urine discharge.

18 Claims, 16 Drawing Sheets

PARTIAL-LENGTH INDWELLING URINARY CATHETER PERMITTING SELECTIVE URINE DISCHARGE

CROSS-REFERENCE TO RELATED APPLICATIONS

This is a division of U.S. patent application for a Partial-Length Indwelling Urinary Catheter and Method Permitting Selective Urine Discharge, Ser. No. 11/246,801, filed Oct. 7, 2005, now U.S. Pat. No. 7,662,145, issued Feb. 16, 2010, which is a continuation-in-part of U.S. patent application for a Partial-Length Indwelling Prostatic Catheter Using Coiled Inflation Tube as an Anchor and Methods of Draining Urine and Flushing Clots, Ser. No. 10/665,742, filed on Sep. 17, 2003, now U.S. Pat. No. 7,766,899, issued Aug. 3, 2010, both of which were filed by some of the inventors hereof and assigned to the assignee hereof.

FIELD OF THE INVENTION

This invention relates to a partial-length indwelling urinary catheter and the use of such a urinary catheter. More particularly, the present invention relates to a new and improved partial-length indwelling catheter that permits the user to selectively open a passageway for the drainage of urine through an obstructed prostatic urethra or a constricted external urinary sphincter muscle under conditions of urinary tract retention and to accommodate a moderate range of differences in position within the urinary tract.

BACKGROUND OF THE INVENTION

Prostate problems, such as benign prostate hyperplasia (BPH) and malignant prostate cancer, are common occurrences among older men. The effects of these diseases are generally accompanied by swelling or enlargement of the prostate gland. Apart from the life-threatening aspects of malignant prostate cancer, the everyday symptoms and effects of these diseases are usually troublesome. One such problem relates to the ability to control and achieve normal urine discharge. When the prostate gland enlarges to the extent that it obstructs the prostatic urethra through the prostate gland, considerable difficulties arise in discharging urine at will. Such difficulties are typically referred to as urinary tract retention. Urinary tract retention can be either acute or chronic.

Surgical treatments are available for relieving urinary tract retention caused by an obstruction of the prostatic urethra. One such treatment is a transurethral resection of the prostate (TURP). A TURP procedure involves surgically resecting tissue from the prostate gland to eliminate or reduce the obstruction or restriction. Surgical operations offer a high probability of an excellent clinical outcome, but they are associated with a high degree of morbidity. Alternative treatments with milder side-effects include transurethral microwave thermotherapy (TUMT), radio frequency needle ablation (TUNA), interstitial laser and hot water induced thermotherapy (WIT). All of these alternative treatments involve heating the obstructive prostatic tissue until the tissue is destroyed or damaged. Thereafter, the destroyed or damaged tissue sloughs off, is absorbed in the body, and otherwise results in an enlargement of the urinary passageway through the prostate gland. The enlargement of the urinary passageway through the prostate gland eliminates or relieves the obstruction and permits better urine flow.

Another form of urinary tract retention results from a weak bladder. A weak bladder condition results when the muscle that surrounds the bladder does not contract and compress the bladder sufficiently to create enough fluid pressure on the urine within the bladder to dilate the orifice in the external urinary sphincter muscle in males and establish a substantial flow of urine into a urinary canal which leads to the exterior of the body. Males have two urinary sphincter muscles: an internal urinary sphincter muscle at the bladder neck or junction of the urethra with the bladder, and an external urinary sphincter muscle at the downstream point where the prostatic portion of the urethra exits from the prostate gland into the urinary canal through the penis.

Under normal conditions when urine is not discharged, both urinary sphincter muscles are constricted to close their orifices and prevent the flow of urine through the urethra. The muscle surrounding the bladder relaxes while the bladder is naturally filled with urine. To urinate, the muscle surrounding the bladder contracts automatically to create fluid pressure on the urine within the bladder. Pressure from the urine is applied to the constricted internal urinary sphincter muscle and is sensed by the brain. The orifice through the internal urinary sphincter muscle is voluntarily dilated to pass urine from the bladder into the prostatic urethra. However, if the muscle surrounding the bladder does not apply sufficient pressure on the urine, there is insufficient fluid pressure on the normally-constricted external urinary sphincter muscle to cause it to dilate or open. The external urinary sphincter muscle opens in response to the fluid pressure conducted through the prostatic urethra. Under circumstances of insufficient fluid pressure, the external urinary sphincter muscle will not dilate or will dilate only slightly, thereby restricting or preventing urine discharge. The inability to empty the bladder of urine can lead to serious health problems and death.

In those cases where the diseased prostate gland cannot be treated by a TURP or by a heat treatment, and in those cases where a weak bladder prevents or restricts urine flow, it is necessary for a mechanical fluid passageway to be established from the bladder. The most prevalent mechanical way to open the external urinary sphincter muscle is to insert a full-length catheter. The full-length urinary catheter extends from the exterior opening of the penis through the entire length of the urinary tract into the bladder. The full-length catheter forms a tubular stent which permanently holds the urinary sphincter muscle open, thereby preventing it from closing and restricting the flow of urine. In some cases, the patient is taught to insert a full-length catheter whenever urination is necessary. In other cases, where the patient cannot insert the full-length catheter himself, medical personnel insert an indwelling full-length catheter in the urinary tract where it must remain. In some cases, the full-length catheter must be used for the remainder of the individual's life.

TURP and the prostate heat treating techniques cause temporary side effects, for example inflammation and swelling of the prostate. The swelling may be so great as to obstruct the passage of urine through the surgically-treated prostate gland. Direct contact from urine can aggravate the inflammation and increase the risk of infection to the viable but nevertheless raw, tender and swollen tissue of the prostate gland after a TUMT or a heat treatment. These side effects of a TUMT or heat treatment usually require the patient to use an indwelling urine drainage catheter for a few days up to several weeks following the procedure to permit urination while the swelling subsides and the tissue of the prostate gland heals or stabilizes.

Because a full-length urinary drainage catheter provides a continuously open interior urine flow passageway between the bladder and the exterior opening of the penis, a clamp or other mechanical valve must be used at the exterior of the body to control the urine flow from the catheter. The clamp or valve is opened to drain the urine from the bladder and is closed to terminate urine flow from the bladder. Alternatively, a reservoir may be attached to the end of the catheter to collect the discharged urine, in which case the mechanical valve or clamp may not be used.

The extension of the catheter out of the exterior opening of the penis, the presence of the clamp or valve and the presence of the reservoir cause discomfort, are awkward to deal with and may be embarrassing. The full-length urinary catheter may create limitations from a social standpoint and almost always creates quality of life issues which must be confronted. Sexual activity is impossible. An increased risk of infection also results.

Because of the quality of life and social issues associated with full-length urinary catheters, partial-length indwelling catheters have been developed. Partial-length indwelling catheters typically extend from the bladder partially along the prostatic urethra, but not along the entire length of the urinary tract from the bladder to the exterior opening of the penis. The typical partial-length indwelling catheter extends from the bladder through the prostatic urethra to an upstream position adjacent to the external urinary sphincter muscle. The reduced length permits the external urinary sphincter muscle to control urine flow in a more natural manner, while still bypassing most of the urine flow around the swollen, obstructed or raw prostate gland.

Keeping a partial-length indwelling catheter in the proper position is essential. The short length may allow the catheter to move completely into the bladder or move out of the bladder into the urethra and the urinary canal. Either type of unintended movement may require serious medical intervention to correct.

A partial-length urinary catheter typically uses an inflatable balloon or other form of anchor at its end which is within the bladder. The balloon or anchor is expanded or enlarged within the bladder. The expanded or enlarged balloon or anchor contacts the bladder neck at the entrance to the urethra and prevents the partial-length catheter from moving out of the bladder and into the urethra. Another downstream anchor is typically attached to the partial-length of catheter to prevent the catheter from moving in the opposite direction into the bladder. The downstream anchor is positioned downstream from the external urinary sphincter muscle and is connected to the partial-length catheter with a short length of thread-like material. The thread-like material extends through the orifice of the external urinary sphincter muscle between the downstream anchor and the partial-length indwelling catheter. The catheter and the downstream anchor are therefore positioned on opposite sides of the external urinary sphincter muscle. The normal constricted state of the external urinary sphincter muscle restrains the downstream anchor and prevents the partial-length catheter from moving into the bladder.

The external urinary sphincter muscle is able to constrict around the thread-like material to stop urine flow and is able to dilate to permit the flow of urine. In this matter, the natural functions of the external urinary sphincter muscle control the discharge of urine. The clamps, valves and reservoirs used with a full length catheter, as well as the self-consciousness, embarrassment and social problems and difficulties caused by these devices, are avoided entirely by using a partial-length indwelling catheter.

Despite the advantages and benefits of a partial-length indwelling catheter, a partial-length indwelling catheter is not effective to overcome the urine discharge problems caused by a weak bladder. The partial-length indwelling catheter terminates upstream of the external urinary sphincter muscle. Although the fluid pressure within the bladder is communicated through the partial-length indwelling catheter to the external urinary sphincter muscle, the relatively low fluid pressure from the weak bladder is insufficient to cause the external urinary sphincter muscle to open. It is for this reason that a partial-length indwelling catheter is not effective in permitting control over urine drainage under weak bladder conditions. A full-length urinary drainage catheter is required for urine drainage under weak bladder conditions and under conditions caused by some neurogenic disorders.

A partial-length indwelling catheter may also be of limited prophylactic value after a TUMT or heat treatment. The downstream end of the partial-length indwelling catheter may not immediately adjoin the external urinary sphincter muscle, but instead, because of differences in physiological length of the prostatic urethra in different males, may terminate a short distance before the external urinary sphincter muscle. This small gap between the downstream end and the external urinary sphincter muscle may swell to the point where it restricts urine flow through the prostate gland after a TUMT or other heat treatment. Similarly, the enlargement of the prostate gland due to BPH or other disease may also extend into the gap between the downstream end of the partial-length indwelling catheter and the external urinary sphincter muscle. Under such obstructive circumstances, the partial-length indwelling catheter is not effective in permitting urine discharge, thereby requiring a full-length urinary drainage catheter to be used instead of the more desirable partial-length indwelling catheter.

SUMMARY OF THE INVENTION

The invention overcomes the problems of urine discharge under conditions of urinary tract retention due to a prostatic urethra obstruction arising from swelling of the prostate gland caused by disease or after surgical treatment, or arising from a weak bladder or neurogenic disorder, as well as under conditions of moderate differences in position and urinary tract physiology. The benefits and other desirable aspects of the invention allow the user to discharge urine at will and avoid the need to use a less-desirable full-length catheter.

The present invention involves a partial-length indwelling catheter for draining urine in a male human from the bladder through the prostate gland and through the orifice in the external urinary sphincter muscle and into the urinary canal which ends at the exterior opening of the urinary canal.

In general terms, use of the partial-length indwelling catheter involves positioning the catheter in a normal position in which a distal end of the catheter is located within the bladder and a proximal end of the catheter is located at a position distally adjacent to and upstream of the external urinary sphincter muscle, anchoring the catheter to resist proximal movement from the normal position, conducting urine from the bladder through an interior passageway of the catheter which extends between the distal end and the proximal end of the catheter, and selectively displacing the proximal end of the catheter in a proximal and downstream direction from the normal position through an orifice in the external urinary sphincter muscle to conduct urine from the bladder through the interior passageway within the catheter and through the external urinary sphincter muscle into the urinary canal, thereby draining or discharging urine from the bladder.

The use of the catheter may also involve some or all of the following features. The proximal end of the catheter is displaced in the distal direction through the orifice of the external urinary sphincter muscle after urine has been drained from the bladder. The normal constriction of the orifice through the external urinary sphincter muscle is relied on to prevent urine drainage from the distal end of the catheter into the urinary canal while the catheter is in the normal position. A control cord is extended from the catheter through the orifice of the external urinary sphincter muscle and through the urinary canal to a position outside of the exterior opening, and the control cord is moved to selectively displace the proximal end of the catheter in a proximal direction from the normal position through the orifice of the external urinary sphincter muscle. The proximal end of the catheter is displaced in a proximal direction from the normal position by moving the entire catheter in the proximal direction or by moving an extendable proximal end portion of the catheter in the proximal direction. The catheter is anchored to resist distal as well as proximal movement from the normal position.

In general terms, the partial-length indwelling catheter has a main body with a distal end and a proximal end. The main body has a length sufficient to establish a normal position in which the distal end is within the bladder and the proximal end is distally adjacent to and upstream of the external urinary sphincter muscle. The main body defines an interior passageway extending from the distal end to the proximal end. The interior passageway communicates with the interior of the bladder. A distal anchor element is connected to the distal end of the main body. The distal anchor element is expandable in size to contact the bladder neck adjacent to the opening of the prostatic urethra into the bladder to restrain the main body against proximal movement from the normal position. A control element is connected at a distal end to the main body and has a length sufficient to extend through the orifice of the external urinary sphincter muscle and through the urinary canal to a position outside the exterior opening. The control element transfers force from its proximal end to the main body to selectively displace the proximal end of the catheter in a proximal direction from the normal position through the orifice of the external urinary sphincter muscle and thereby conduct urine from the bladder through the interior passageway and into the urinary canal at a position proximal and downstream of the external urinary sphincter muscle.

The partial-length indwelling catheter may also include some or all of the following features. The control element may include a control cord which is connected to the main body to transfer pulling force that is sufficient to compress the distal anchor element against the bladder neck and move the entire catheter in the proximal direction to thereby displace the proximal end of the catheter from the normal position in a proximal direction through the orifice of the external urinary sphincter muscle. The distal anchor element may include an inflatable balloon which can be inflated with fluid, and the inflatable balloon is compressed against the bladder neck when the entire catheter is moved in the proximal direction to thereby displace the proximal end of the catheter from the normal position in a proximal direction through the orifice of the external urinary sphincter muscle. The force of compressing the inflatable balloon against the bladder neck to displace the proximal end of the catheter in the distal direction through the orifice of the external urinary sphincter muscle returns the main body to the normal position after releasing the force on the control cord. The main body may include an extendable proximal end portion. The control element is connected to the extendable proximal end portion to move the extendable proximal end portion in a proximal direction from the normal position through the orifice of the external urinary sphincter muscle. A bias element is connected between the extendable proximal end portion and the main body to return the extendable proximal end portion from extending through the orifice of the external urinary sphincter muscle upon ceasing application of pulling force on the control cord. The extendable proximal end portion of the main body may comprise a tube member which is telescopically movable relative to the main body or a flexible sleeve member which is expandable relative to the main body. The control element or cord transfers pulling force which is sufficient to move the extendable proximal end portion of the main body in the proximal direction relative to the main body and through the orifice of the external urinary sphincter muscle. A proximal anchor element is connected to the main body and is located at a position on the proximal side of the external urinary sphincter muscle when the distal anchor element contacts the bladder neck. The proximal anchor element restrains the main body against distal movement from the normal position.

Additional features of the catheter may include some or all of the following. The distal anchor element comprises an inflatable balloon which is attached to the main body. An inflation tube is connected to the main body and has a length sufficient to extend from the main body through the orifice in the external urinary sphincter muscle. The inflation tube communicates fluid for expanding the balloon. A proximal anchor element of the catheter includes a coiled section of the inflation tube within the urinary canal at a position proximal and downstream of the external urinary sphincter muscle when the orifice through the external urinary sphincter muscle is constricted.

A more complete appreciation of the scope of the present invention and the manner in which it achieves its significant improvements can be obtained by reference to the following detailed description of presently preferred embodiments taken in connection with the accompanying drawings, which are briefly summarized below, and by reference to the appended claims.

DETAILED DESCRIPTION

Figure 1:
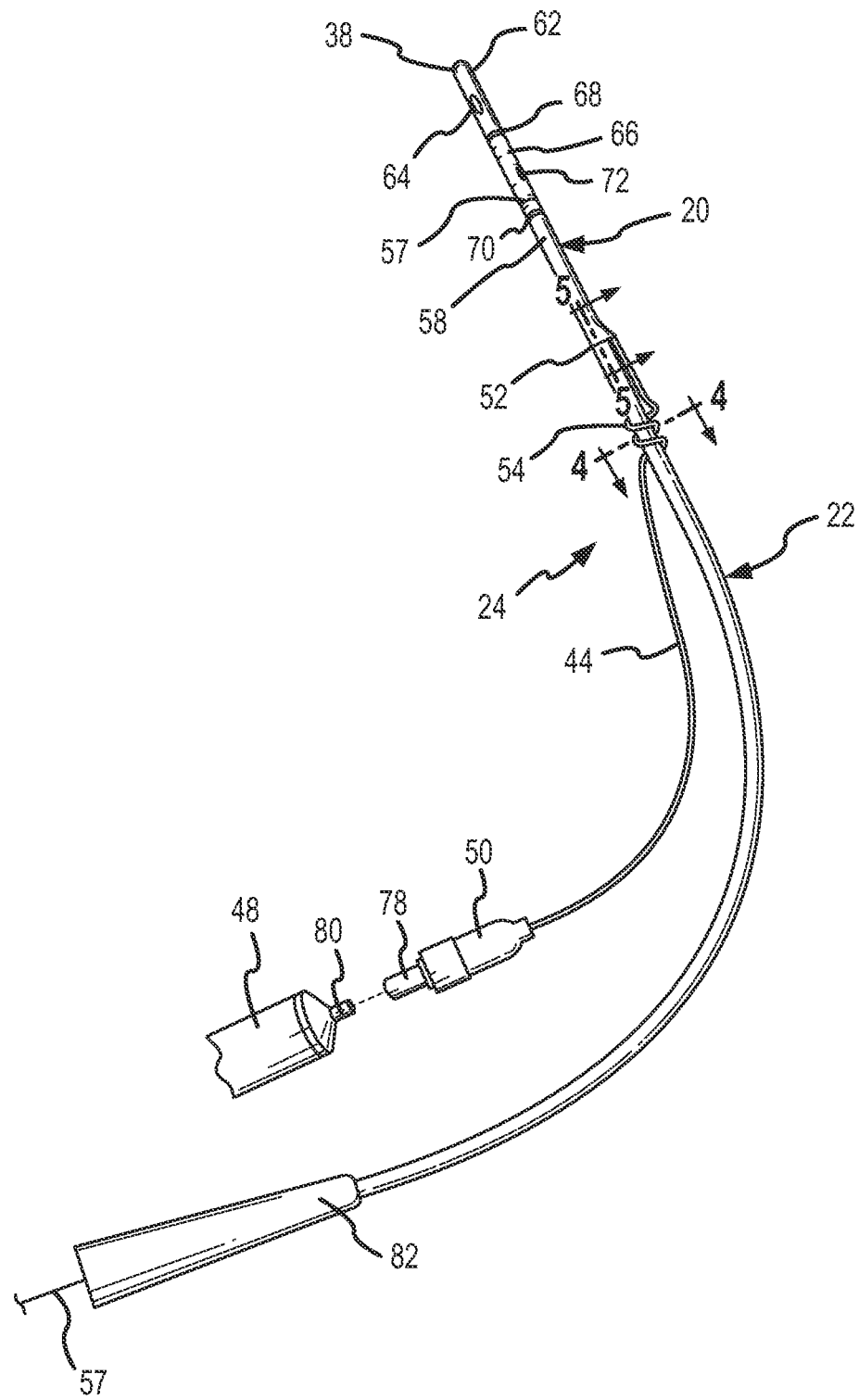
FIG. 1 is a perspective view of a partial-length indwelling prostatic catheter which incorporates the present invention, shown attached to an insertion tool and used with a syringe.
Figure 2:
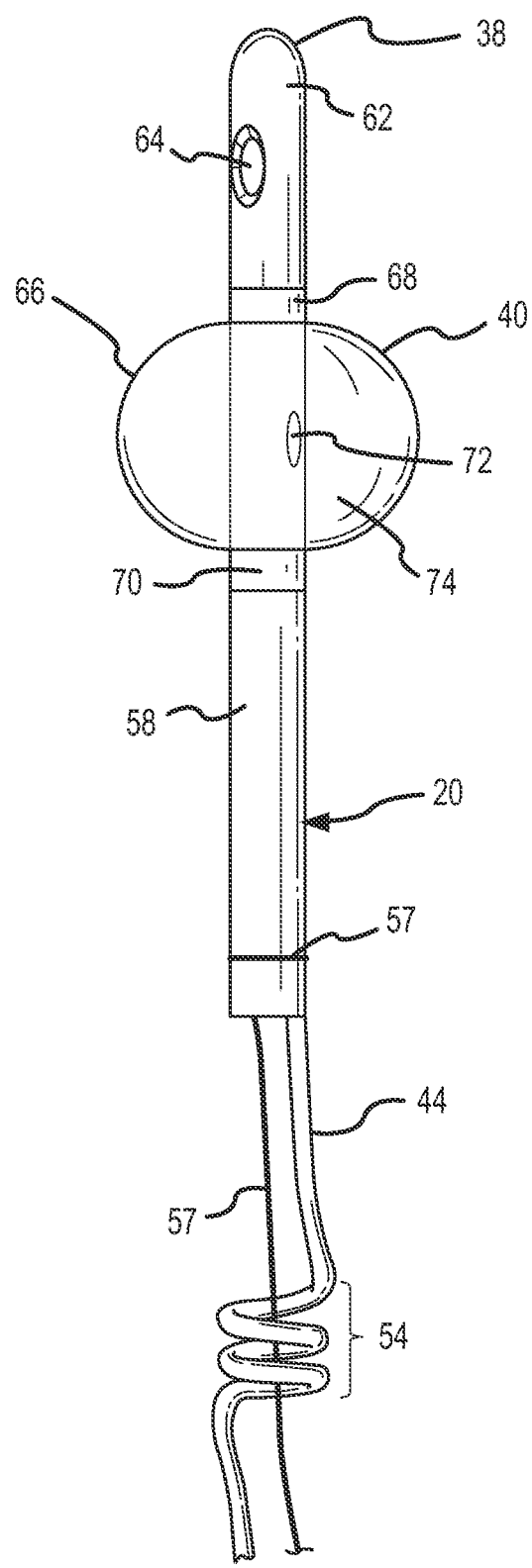
FIG. 2 is an enlarged perspective view of the catheter shown in FIG. 1 with the insertion tool removed and with a balloon of the indwelling catheter expanded.

One embodiment of a partial-length indwelling catheter 20 which incorporates the present invention is shown in FIG. 1. The indwelling catheter 20 is connected to an insertion tool 22 to form a catheter-tool assembly 24, which allows the catheter 20 to be inserted into a urinary tract of a human being, such as a urinary tract 26 of a male human shown in FIG. 6. Once inserted, the insertion tool 22 is disconnected or separated from the indwelling catheter 20 to leave the catheter 20 dwelling or remaining within the urinary tract, to extend through a prostatic urethra 28 within a prostate gland 30 of a male human being shown in FIGS. 6-9, 12 and 15. In its indwelling use position shown in FIG. 8, the catheter 20 conducts urine from a bladder 32 through the prostatic urethra 28 within the prostate gland 30 to a position slightly upstream of an external urinary sphincter muscle 34.

Figure 6:
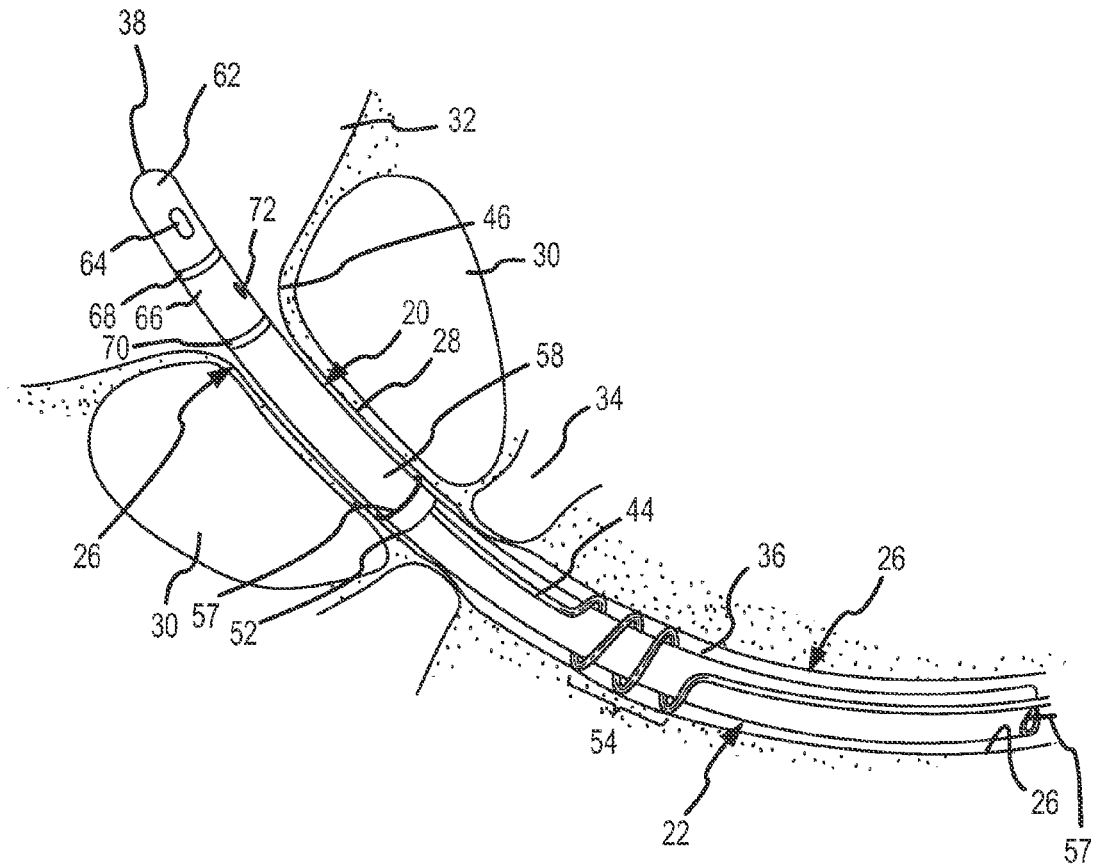
FIG. 6 is a perspective view of the indwelling catheter and a portion of the insertion tool shown in FIG. 1, shown inserted within a urethra, an external urinary sphincter muscle, a prostatic urethra and a bladder of a urinary tract of a male human being, with the physiology generally illustrated in cross-section.
Figure 7:
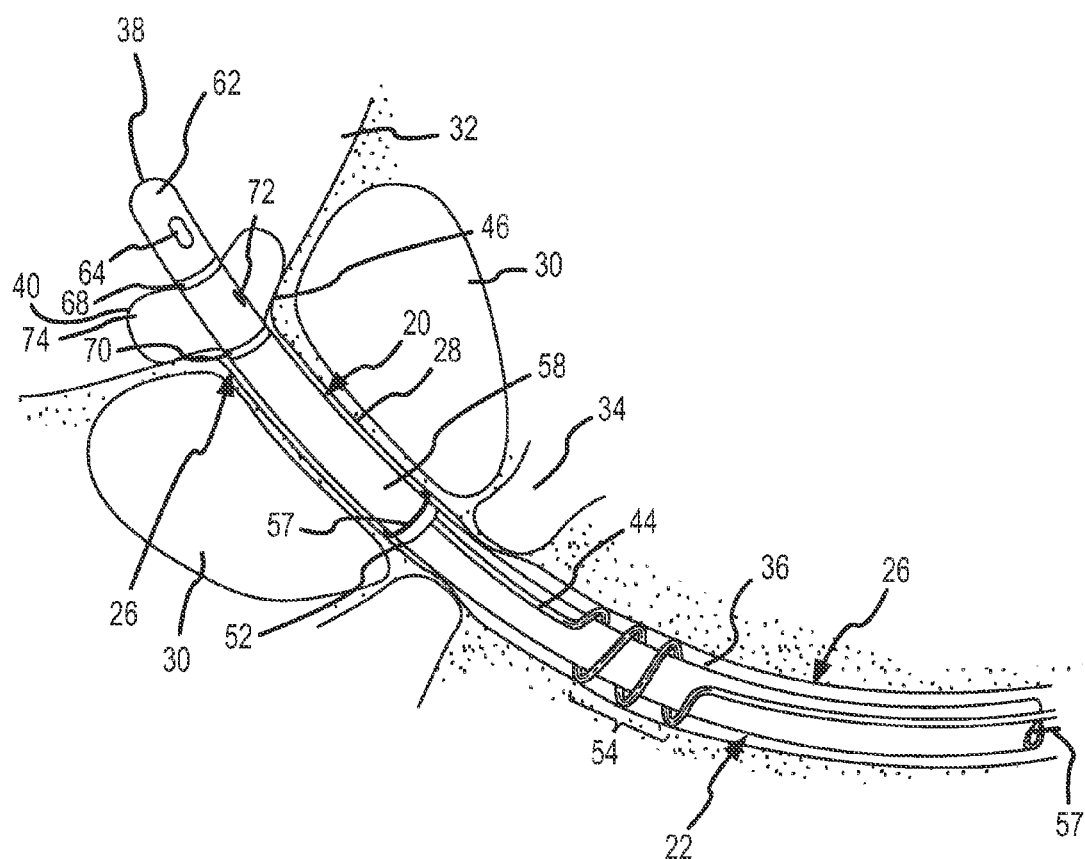
FIG. 7 is an illustration similar to FIG. 6 showing the balloon inflated within the bladder.

The indwelling catheter 20 is pushed into the urinary tract 26 with the insertion tool 22 until a distal end 38 of the indwelling catheter 20 enters the bladder 32 as shown in FIG. 6. A balloon 40 on the indwelling catheter 20 is inflated with fluid conducted through an inflation passageway 42 of an inflation tube 44 until the balloon 40 is larger in diameter than a neck 46 of the bladder 32 surrounding the prostatic urethra 28, as shown in FIG. 7. The inflation fluid may be gas, such as air, or liquid such as saline solution. The balloon 40 is preferably inflated from an inflation pump, such as a syringe 48, which is connected to a valve assembly 50 at the end of the inflation tube 44 (FIG. 1). Once the balloon 40 has been inflated, the insertion tool 22 is pulled backwards until the inflated balloon 40 is seated on the bladder neck 46. When seated on the bladder neck 46, the balloon 40 prevents the indwelling catheter 20 from moving out of the bladder 32 through the external urinary sphincter muscle 34 and into the urinary canal 36.

Figure 8:
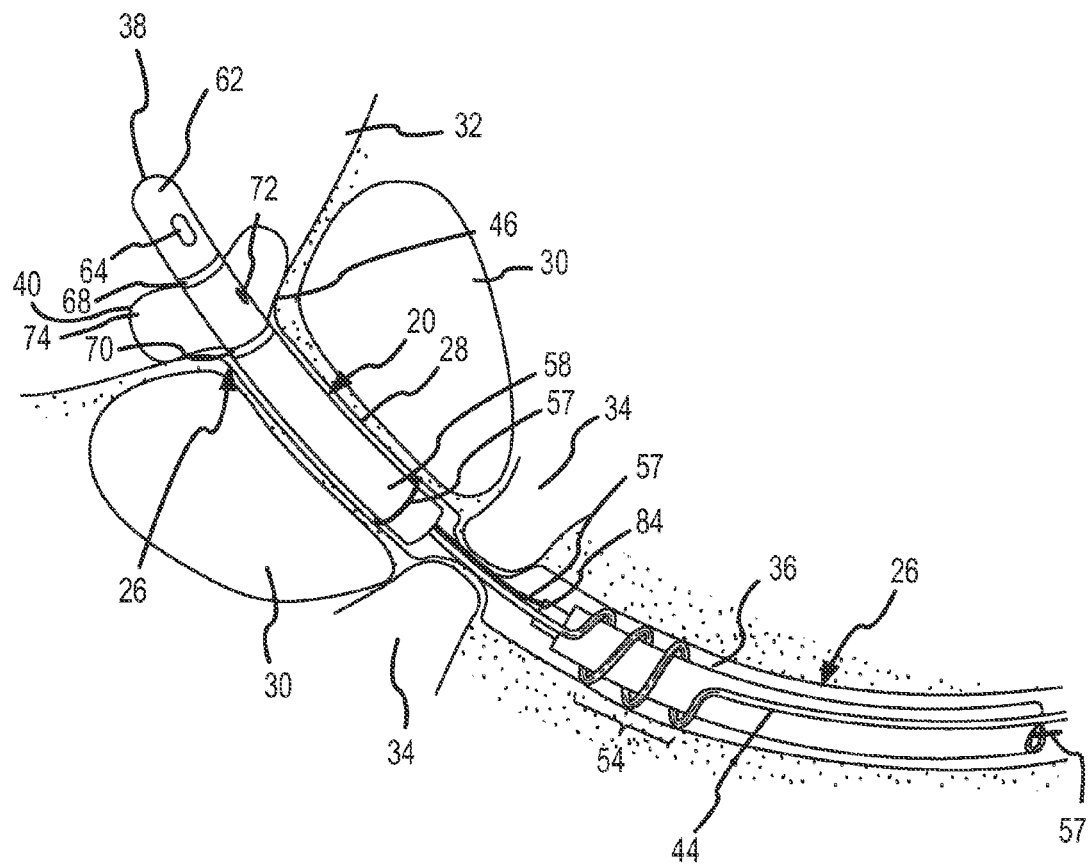
FIG. 8 is an illustration similar to FIGS. 6 and 7 showing separation of the insertion tool from the indwelling catheter.

Continued withdrawal movement of the insertion tool 22 causes it to separate from the catheter 20 at a separable connection 52 (FIG. 1) between the indwelling catheter 20 and the insertion tool 22 as shown in FIG. 8, thereby leaving the indwelling catheter 20 in its final, indwelling position shown in FIG. 8. The insertion tool 22 is thereafter withdrawn and removed from within the urinary canal 36. The inflation tube 44 remains within the urinary canal 36.

The relative terms "proximal" and "distal" are used herein in relation to the catheter and the medical practitioner who inserts the catheter into the urinary tract 26 at the exterior opening of the urinary canal 36. Accordingly, the portions of the catheter 20 which are the most internal within the patient are referred to as "distal," and the portions of the catheter 20 which are closest to the exterior opening of the urinary canal 26 are referred to as "proximal." The "distal" portions of the catheter are therefore located more interiorly within the urinary tract 26 than are the "proximal" portions of the catheter. The "distal" portions of the catheter are upstream relative to the normal direction of urine flow and the "proximal" portions of the catheter are downstream relative to the normal direction of urine flow. The same reference convention is also used to describe relative positions of the male urinary tract physiology with which the catheter interacts. As an example of this reference convention, the balloon 40 is located near the "distal" end of the catheter 20, and a "distal" end of the inflation tube 44 connects to a "proximal" end of a main body 58 of the catheter 20 at a location upstream or "distal" of the external urinary sphincter muscle 34, and urine from the bladder 32 will be drained through an orifice from the "distal" side to the "proximal" side of the external urinary sphincter muscle and then into the urinary canal 36.

The inflation tube 44 is formed with a permanently helically coiled section 54 shown in FIGS. 1-3 and 6-9. The coiled section 54 is resilient both in the transverse dimension and in the longitudinal dimension. The inflation tube 44 has sufficient strength to maintain the coiled section 54 in the coiled configuration within the urinary canal 36 after removal of the insertion tool 22. Because of the resiliency of the coiled section 54, the coiled section 54 presses against the interior of the urinary canal 36. By resiliently pressing against the interior of the urinary canal 36, the coiled section 54 also minimizes discomfort to the patient or irritation to the urinary canal 36. The coiled section 54 is not disruptive to the flow of urine through the urinary canal 36 because the coiled section 54 provides a fluid-flow path through an open center of the coils.

Located slightly proximally of the urinary sphincter muscle 34, the coiled section 54 of the inflation tube 44 functions as an anchor element to assist in holding the indwelling catheter 20 in the urinary tract 26 in the position shown in FIG. 8. The coiled section 54 prevents the indwelling catheter 20 from moving distally from the position shown in FIG. 8, as a result of the coils of the coiled section 54 contacting a constriction in the urinary tract caused by constriction of the orifice of the sphincter muscle 34. The coiled section 54 contacts the constriction to resist the distal movement of the indwelling catheter 20 and to prevent it from moving into the bladder 32. The inflated balloon 40 also functions as an anchor by creating a restriction at the distal end 38 of the indwelling catheter 20 to prevent it from moving proximally along the urinary tract 26 and out of the urinary canal 36. With the inflated balloon 40 located at the distal end of the indwelling catheter 20 and the coiled section 54 located on the proximal side of the sphincter muscle 34, the indwelling catheter 20 is anchored to resist movement either into or out of the bladder 32 and out of the prostatic urethra.

With the indwelling catheter 20 in the normal use position anchored by the balloon 40 and the coiled section 54, urine or other fluid from the bladder 32 is able to flow through a urine drainage channel or interior passageway 56 (FIG. 3) in the indwelling catheter 20 and out of the proximal end of the catheter 20, which is normally located adjacent to the dilated external urinary sphincter muscle 34. Provided that there is no obstruction of the prostatic urethra between the proximal end of the indwelling catheter 20 and the external urinary sphincter muscle 34, as could occur from prostate gland disease or from swelling following surgical treatment to the prostate gland 30, and provided that the bladder 32 is not weakened and is able to supply adequate fluid pressure on the urine, the fluid pressure will dilate the orifice through the external urinary sphincter muscle to allow the urine to flow through the dilated external urinary sphincter muscle 34 and into the urinary canal 36. However, such conditions do not require the use of a catheter in accordance with the present invention. The present invention is intended to be used to overcome prostatic urethra blockage between the proximal end of the indwelling catheter 20 and the external urinary sphincter muscle 34, resulting from prostate gland disease or from swelling following surgical treatment of the prostate gland, and to overcome a weak bladder condition or other neurogenic disorder where insufficient fluid pressure is available from the bladder 32 to open the external urinary sphincter muscle 34.

Figure 9:
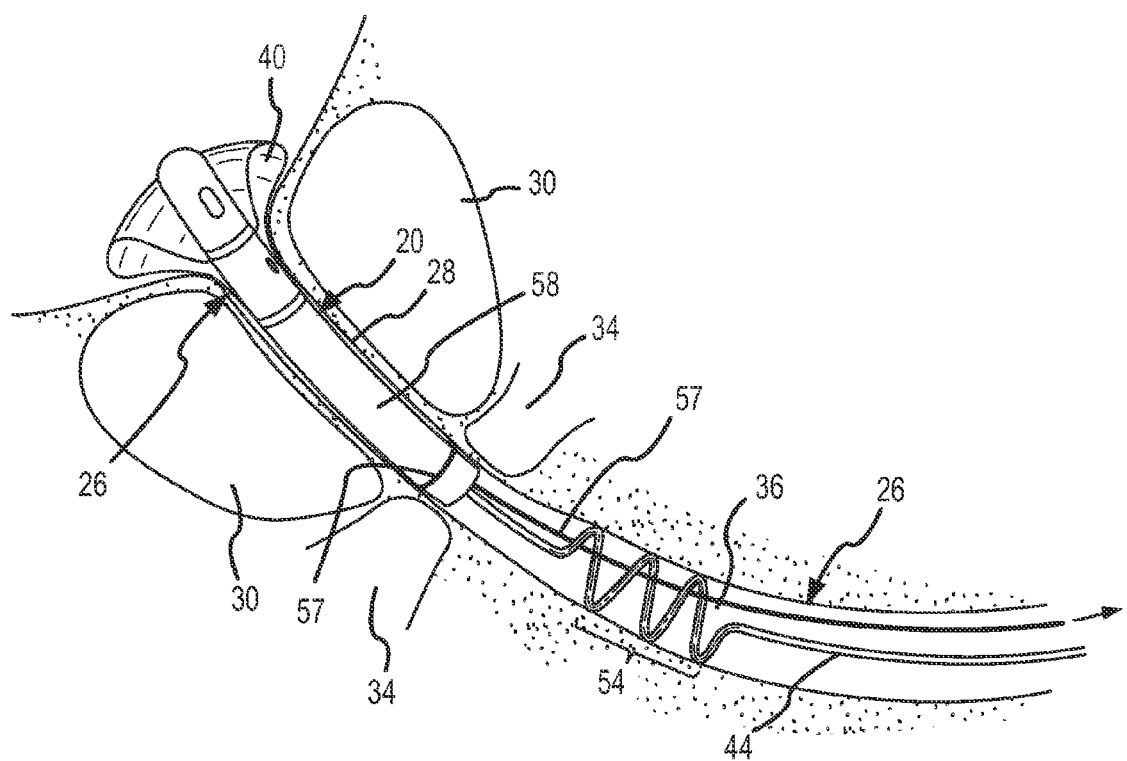
FIG. 9 is an illustration similar to FIGS. 6-8 showing use of the indwelling catheter when discharging urine through an orifice of the external urinary sphincter muscle.

To open a urine drainage passageway through an obstructed prostatic urethra or under weak bladder conditions, a control element, such as a control cord 57, is used. The control cord 57 may take the form of a relatively thin synthetic or natural line which does not stretch appreciably when pulled. The control cord 57 is connected at one end to a main body 58 of the indwelling catheter 20 (FIGS. 2 and 3), and the other end extends through the urinary canal 36 beyond the point where the canal 36 opens from the penis. Pulling the control cord 57 at a position exterior of the body moves the main body 58 proximally through the area of the obstructed prostate gland or prostatic urethra immediately upstream or distal of the external urinary sphincter muscle 34. The proximal movement of the main body 58 opens the orifice of the external urinary sphincter muscle 34, as shown in FIG. 9. Once the proximal end of the main body 58 extends through the obstructed prostatic urethra area and into the orifice through the external urinary sphincter muscle 34, urine is drained from the bladder 32 through the interior passageway 56 within the catheter 20 and into the urinary canal 36 downstream of the external urinary sphincter muscle 34. The urine thereafter drains naturally from the urinary canal 36 and out of the exterior opening of the penis.

The balloon 40 is sufficiently flexible to expand and compress around the tissue of the bladder neck 46 when the control cord 57 is pulled. The tissue of the bladder neck 46 is also compressed from the pressure of the compressed balloon 40 which is forced against the bladder neck 46, as shown in FIG. 9. As a result of its compression and expansion, the balloon 40 does not inhibit the main body 58 from moving in the proximal direction a sufficient distance to extend through the obstructed prostatic urethra and through the orifice of the external urinary sphincter muscle, under the pulling force applied by the control cord 57, as shown in FIG. 9.

Selectively extending the main body 58 of the catheter 20 permits the user to discharge urine from his bladder 32 at will by pulling on the control cord 57, despite the fact that the bladder may be so weak that the orifice through the external urinary sphincter muscle 34 cannot be opened naturally. Under weak bladder conditions, the main body 58 must be pulled sufficiently to extend the proximal end of the main body into the orifice of the external urinary sphincter muscle 34 and force open the orifice through the muscle 34. When the prostate gland is swollen in the area between the proximal end of the main body 58 and the external urinary sphincter muscle 34, but the fluid pressure from the bladder is otherwise sufficient to dilate the external urinary sphincter muscle 34, the main body 58 must be pulled sufficiently to extend through the obstruction. Under these circumstances it is not necessary to force open the orifice through the external urinary sphincter muscle, because sufficient pressure from the bladder is available to dilate the muscle 34.

After urine discharge is complete, the pulling force on the control cord 57 is released. The compression of the balloon 40 which occurred when the main body 58 was pulled by force from the control cord 57 and the compression of the tissue at the bladder neck 46 as a result of contact from the compressed balloon 40, apply sufficient longitudinal force to move or translate the main body 58 of the catheter 20 back to its normal position, shown in FIG. 8. Once the normal position is achieved, the fluid within the balloon 40 is no longer compressed against the bladder neck 46. Retraction of the catheter 20 to its normal position (FIG. 8) allows the external urinary sphincter muscle to constrict around the length of inflation tube 44 and the control cord 57 between the proximal end of the indwelling catheter 20 and the coiled section 54, thereby preventing further urine drainage through the urethra at the external urinary sphincter muscle 34. A weak bladder condition does not adversely affect the ability of the external urinary sphincter muscle 34 to constrict and stop the flow of urine through the urinary canal 36. Thus, the catheter 20 allows the external urinary sphincter muscle 34 to prevent urine discharge in a natural manner, while the selective extension of the proximal end of the main body 58 overcomes the inability to discharge urine under prostatic obstruction, weak bladder and certain neurogenic disorder conditions.

The main body 58 of the indwelling catheter 20 is preferably made from silicone rubber. The main body 58 has a generally cylindrical exterior shape. The main body 58 includes a sidewall 60 (FIG. 3) which defines the passageway 56 through the main body 58. An end piece 62 is either attached to or integral with the main body 58 at the distal end 38 of the catheter 20. The end piece 62 has a tip configuration adapted to facilitate insertion of the catheter 20 and the insertion tool 22 into the urinary tract 26. At least one and preferably a pair of urine inlet openings 64 are formed through the end piece 62. The openings 64 communicate between the exterior of the end piece 62 and the passageway 56 of the main body 58. Urine from the bladder 32 flows through the openings 64 and into and through the passageway 56 to the proximal end of the main body 58.

The balloon 40 is formed by a flexible sleeve 66 of relatively thin, flexible, expandable, usually-transparent and nonporous material which is attached with fluid-tight seals 68 and 70 around the exterior of the main body 36. A first fluid-tight seal 68 is located slightly proximally of the distal end of the main body 58 where the end piece 62 is attached, and a second fluid-tight seal 70 is spaced proximally along the main body 58 from the first seal 68 by a distance approximately equal to the axial length of the flexible sleeve 66. The fluid-tight seals 68 and 70 are preferably formed by attaching the flexible sleeve 66 to the main body 58 with an adhesive or by thermal welding.

The flexible sleeve 66 is positioned over the top of and extends axially on opposite sides of an opening 72 from the main body 58. The fluid-tight seals 68 and 70 are located distally and proximally of the opening 72, respectively. Fluid is introduced into a volume 74 at the exterior of the main body 58 between the fluid-tight seals 68 and 70 and within the flexible sleeve 66, causing the flexible sleeve 66 to expand outward and create the balloon 40.

Figure 3:
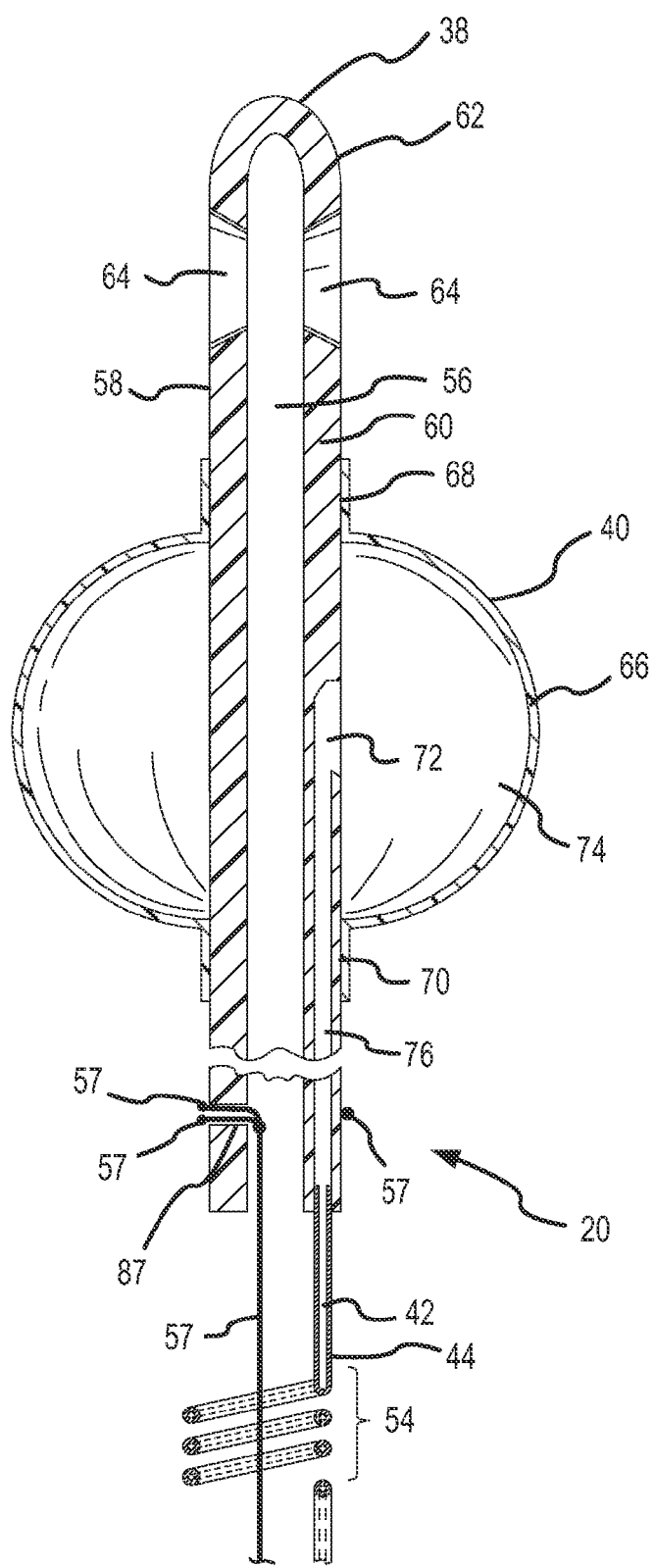
FIG. 3 is an enlarged longitudinal cross-section view of the catheter shown in FIG. 2, taken substantially in a longitudinal axial plane with a portion broken out.
Figure 5:
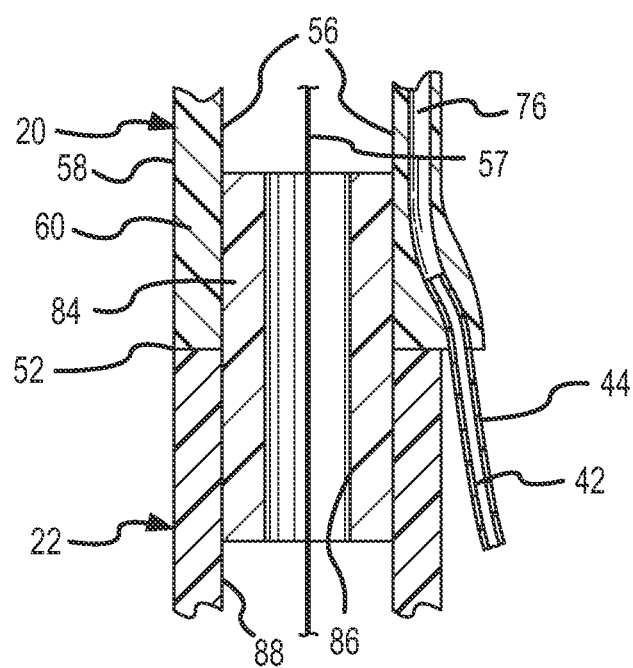
FIG. 5 is an enlarged partial longitudinal axial cross-section view of a separable connection of the indwelling catheter-insertion tool assembly shown in FIG. 1, taken substantially in the plane of line 5-5 shown of FIG. 1.

An inflation conduit 76 communicates with the opening 72, as shown in FIG. 3. The inflation conduit 76 is formed within the sidewall 60 of the main body 58. A distal end of the inflation tube 44 is inserted into a proximal end of the inflation conduit 76, as shown in FIGS. 3 and 5. The fluid is delivered from the syringe 48 (FIG. 1) into the inflation passageway 42 of the inflation tube 44 and flows into the inflation conduit 76, out of the opening 72 and into the volume 74 beneath the flexible sleeve 66, causing the flexible sleeve 66 to expand into the form of the balloon 40.

Inserting the distal end of the inflation tube 44 into the inflation conduit 76, as shown in FIG. 5, allows the inflation tube 44 to bypass or go around the separable connection 52 between the indwelling catheter 20 and the insertion tool 22. A strong fluid-tight bond is formed by attaching the inflation tube 44 into the inflation conduit 76 with an adhesive. The attachment maintains the inflation tube 44 connected to the main body so that pulling on the inflation tube from the exterior of the urinary canal 36 will remove the catheter 20 from the urinary tract 26 without the inflation tube 44 breaking away from the main body 58. In this regard the inflation tube 44 also serves as a tether for the catheter 20. The separable connection 52 shown in FIG. 5 permits fluid communication between the inflation passageway 42 and the inflation conduit 76 to remain intact and fluid tight after the insertion tool 22 has separated from the indwelling catheter 20 while the catheter 20 remains positioned within the urinary tract. The continued integrity of the inflation passageway between the balloon 40 and the valve assembly 50 allows the balloon 40 to be periodically reinflated while the indwelling catheter 20 is in use, if necessary. Periodic reinflation may be necessary as a result of minute leaks in the balloon 40, the valve assembly 50 or the passageways connecting the balloon 40 and the valve assembly 50.

The inflation tube 44 has a length which extends from the main body 58 of the indwelling catheter 20 through the urinary canal 36 to the outside of the human body. The length of the inflation tube 44 is sufficient to position the valve assembly 50 at the exterior of the human body. The inflation tube 44 has sufficient rigidity to prevent the inflation passageway 42 within the tube 44 from collapsing from contact with the tissue of the urinary tract 26, but the rigidity is not so great as to prevent a moderate amount of flexibility in the inflation tube 44. The moderate flexibility of the inflation tube 44 allows it to extend through the typical curves of the urinary tract 26.

The valve assembly 50 is of a conventional construction and includes a receptacle 78 into which a nozzle 80 of the syringe 48 is inserted, as shown in FIG. 1. The valve assembly 50 also includes a conventional internal check valve (not shown) which closes the inflation passageway 42 at the valve assembly 50 when the nozzle 80 is removed from the receptacle 78. In this manner, fluid from within the balloon 40 is prevented from escaping through the inflation passageway 42 when the syringe 48 is disconnected from the valve assembly 50, but the check valve permits fluid from the syringe 48 to inflate the balloon 40 when a plunger (not specifically shown) of the syringe 48 is depressed. Thus, the balloon 40 will remain inflated after the syringe 48 is disconnected from the valve assembly 50. However, should the balloon 40 need to be reinflated or should additional fluid need to be added to expand the balloon 40 during use of the catheter, the syringe 48 is easily connected to the valve assembly 50 for doing so.

As an alternative to the use of the valve assembly 50, the inflation passageway 42 can be sealed at a proximal end after the balloon 40 has been inflated. For example, instead of using the valve assembly 50 to prevent fluid from escaping from the balloon, a knot (not shown) may be formed or tied in the proximal end of the inflation tube 44 at a location spaced proximally from the external opening of the urinary canal 36. The knot seals the inflation passageway 42 and prevents the fluid from escaping through the passageway to maintain the balloon 40 inflated. The inflation tube 42 is cut at a position slightly proximally of the knot. In this alternative configuration, the inflation tube 44 without the valve assembly 50 extends only a modest distance from the open end of the urinary canal 36. Greater comfort and convenience is promoted because there is no sizable apparatus to deal with, such as the valve assembly 50 connected to the proximal end of the inflation tube 44. If the balloon 40 needs to be reinflated or have additional fluid added after the indwelling catheter 20 has been used for some time, the knot can be cut from the end of the inflation tube 44 and a suitable connector attached to allow the syringe 48 to introduce additional fluid. After suitable inflation, another knot can be tied in the remaining proximal portion of the inflation tube 40. Releasing the fluid through the inflation passageway 42 collapses the balloon 40 and allows the catheter 20 to be pulled out of the urinary canal 36 by pulling on the inflation tube 44 and the control cord 57.

The control cord 57 is secured to the main body 58 in a way which prevents the cord 57 from disconnecting from the main body 58 even when significant pulling force is applied to the control cord 57. To securely attach the control cord 57 to the main body 58, as can be understood from FIG. 3, the control cord 57 is passed from the interior passageway 56 of the main body 58 through a hole 87 in the sidewall 60. The control cord 57 is then looped transversely around the exterior of the main body 58 before passing back through the hole 87 to the interior passageway 56 where the control cord 57 is secured to itself. In this configuration, pulling force on the control cord 57 is transferred into force tending to tighten the control cord 57 around the main body 58. The main body 58 is able to withstand the force of the tightening control cord 57 without collapsing when the force on the control cord 57 is sufficient to pull the main body 58 into and open the orifice of the external urinary sphincter muscle 34. This arrangement allows the control cord 57 to pull the indwelling catheter 20 into the external sphincter 34, as shown in FIG. 9, without the control cord 57 damaging or detaching from the main body 58.

Figure 4:
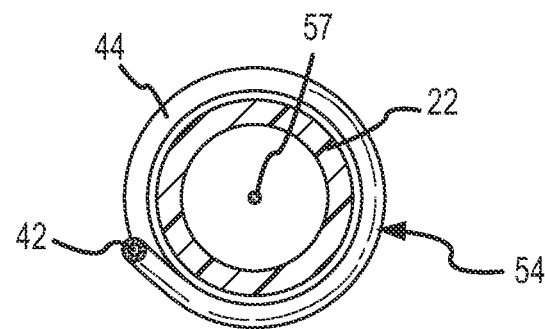
FIG. 4 is an enlarged transverse cross-section view taken substantially in the plane of line 4-4 of FIG. 1.

With the catheter 20 connected to the insertion tool 22, the coiled section 54 extends around the exterior of the insertion tool 22, as shown in FIG. 4, while the control cord 57 extends through the interior passageway 56 of the main body 58 and an interior channel 88 of the insertion tool 22, as shown in FIGS. 5 and 8. By extending around the exterior of the insertion tool 22, the coiled section 54 assists in holding the inflation tube 44 adjacent to the insertion tool 22 while the indwelling catheter 20 and the insertion tool 22 are inserted in the urinary tract 26. The coiled section 54 therefore assists in moving the inflation tube 44 into the urinary tract 26 along with the insertion tool 22. The helically coiled section 54 is loosely wound around the insertion tool 22, thereby allowing the insertion tool 22 to be withdrawn through the center of the coiled section 54 as the insertion tool 22 is disconnected from the indwelling catheter 20.

The insertion tool 22 is a flexible tubular structure and is generally configured similar to the proximal portion of a typical full-length urinary catheter. The insertion tool 22 is at least long enough to extend from outside of the body into the urinary canal 36 and prostatic urethra 28 to a point that will place the indwelling catheter 20 in the final desired use position. The insertion tool 22 is preferably made from silicone rubber, but has sufficient structural integrity to transfer pushing forces supplied on the outside of the body longitudinally along the length of the insertion tool 22, thereby allowing the insertion tool 22 with the attached indwelling catheter 20 to be moved distally into the urinary tract 26. A proximal end of the insertion tool 22 may take the form of a hollow handle 82 or enlargement, by which to grip the insertion tool 22 and apply pushing force to it during insertion in the urinary tract 26.

The separable connection 52 between the insertion tool 22 and the indwelling catheter 20 includes a sleeve 84, shown in FIG. 5. The sleeve 84 is rigidly connected to the distal end of the insertion tool 22 by an adhesive, for example. A distal portion of the sleeve 84 projects beyond the distal end of the insertion tool 22 and into the interior passageway 56 of the catheter 20. The distal portion of the sleeve 84 has an exterior diameter which frictionally fits within the interior passageway 56, and the friction created by the insertion of the sleeve 84 into the interior passageway 56 is sufficient to retain the indwelling catheter 20 to the insertion tool 22 during manipulation of the catheter-tool assembly 24 within the urinary tract 26 during insertion and placement, prior to inflation of the balloon 40. The degree of frictional resistance between the distal end of the sleeve 84 and the main body 58 at the proximal end of the interior passageway 56 is not so great as to prevent the indwelling catheter 20 from separating from the insertion tool 22 once the balloon 40 has been inflated and seated against the bladder neck 46.

The sleeve 84 has a center opening 86 (FIG. 5) which provides a passageway between the interior passageway 56 of the main body 58 and an interior channel 88 of the insertion tool 22. The control cord 57 extends from the proximal end of the main body 58 through the center opening 88 of the sleeve 84 and the interior channel 88 and the handle 82 of the insertion tool 22 and extends out of the proximal end of the handle 82 as illustrated in FIG. 1. When the insertion tool 22 is removed from the indwelling catheter 20, as shown in FIG. 8, the control cord 57 remains in the urethra 36 and extends from the main body 58 proximally to the exterior opening of the urethra to allow the control cord 57 to be grasped on the exterior of the urethra at the penis. A mechanical connector which is capable of convenient disconnection may be used as an alternative to the frictional connection provided by the sleeve 84.

The catheter-tool assembly 24 is inserted and used in the manner illustrated in FIGS. 6-8. As shown in FIG. 6, the catheter 20 and the insertion tool 22 are inserted into the urinary tract 26 through the urinary canal 36, in a manner similar to the way that a conventional full-length urinary catheter would be inserted. The insertion force is applied by pushing on the insertion tool 22 and on the handle 82 attached at its proximal end. Distal movement of the catheter-tool assembly 24 continues until the rounded end piece 62 and a significant distal portion of the indwelling catheter 20 are located in the bladder 32. The insertion is sufficient to assure that the flexible sleeve 66 will be located within the bladder 32. To assure sufficient insertion, it is frequently the case that the distal movement continues until terminated when the end 38 contacts the opposite wall of the bladder 32, thereby assuring that the balloon 40 is within the bladder 32. During insertion in this manner, the coiled section 54, which is wrapped around the insertion tool 22, helps keep the forward or distal portion of the inflation tube 44 aligned with and progressing with the indwelling catheter 20.

Once the catheter-tool assembly 24 has been inserted sufficiently, the balloon 40 is inflated as shown in FIG. 7. Inflation is achieved by connecting the syringe 48 to the valve assembly 50, and depressing the plunger (not shown) of the syringe 48 to force fluid through the inflation passageway 42 of the inflation tube 44, into the inflation conduit 76, through the opening 72 and into the interior volume 74, causing the flexible sleeve 66 to expand into the balloon 40. After the balloon 40 is in the expanded position, the insertion tool 22 is pulled to move the catheter-tool assembly 24 in the proximal direction until the inflated balloon 40 seats against the bladder neck 46.

With the balloon 40 seated against the bladder neck 46, continued proximal movement of the insertion tool 22 causes the separable connection 52 to separate the indwelling catheter 20 from the insertion tool 22, as shown in FIG. 8. The balloon 40 prevents the indwelling catheter 20 from coming out of the urinary tract 26 with the insertion tool 22 because the expanded balloon 40 is larger than the bladder neck 46. The coiled section 54 of the inflation tube 44, being located proximally from the external urinary sphincter muscle 34, prevents the indwelling catheter 20 from moving into the bladder 32. The continued withdrawal of the insertion tool 22 is not inhibited by the coiled section 54, because the body of the insertion tool 22 moves through the interior of the coiled section 54. The length of the inflation tube 44 is sufficient to locate the valve assembly 50 at the exterior of the urinary tract 26. The length of the control cord 57 is also sufficient to locate the proximal end of the control cord 57 at the exterior opening of the urinary tract 26 at the penis.

After the insertion tool 22 is removed as understood from FIG. 8, the balloon 40 remains inflated in the bladder 32, and the proximal end of the main body 58 of the indwelling catheter 20 extends through most of the prostatic urethra 28 but does not extend through the external urinary sphincter muscle 34. The coiled section 54 is located on the opposite or proximal side of the external urinary sphincter muscle 34. In this final position, the balloon 40 prevents the indwelling catheter 20 from moving out of the prostatic urethra 28 and into the urinary canal 36, while the coiled section 54 prevents the indwelling catheter 20 from moving out of the prostatic urethra 28 and into the bladder 32. The inflation tube 44 and the control cord 57 do not interfere with the ability of the urinary sphincter muscle 34 to naturally stop the urine flow by constricting around the inflation tube 44 and control cord 57.

If the catheter 20 is no longer needed, or if it is necessary to periodically replace the indwelling catheter 20, removal is accomplished after deflating the balloon 40. Deflation is accomplished by inserting the syringe 48 into the valve assembly 50 and moving the plunger (not shown) of the syringe 48 outward to withdraw fluid from the inflation passageway 42. The insertion of the syringe 48 in the valve assembly 50 opens the check valve within the valve assembly 50 and allows the fluid to be withdrawn. If the inflation tube 44 has been tied into a knot to avoid use of the valve assembly 50 in the manner described above, the inflation tube 44 may be cut at a location distal of the knot to allow the fluid to escape. The escaping fluid causes the balloon 40 to deflate, and the flexible sleeve 66 moves to a collapsed position (shown in FIGS. 1 and 6) adjacent to the main body 58 of the indwelling catheter 20.

Once the balloon 40 has been deflated, the inflation tube 44 and/or the control cord 57 is/are pulled outward by gripping and pulling on the valve assembly 50 or the proximal end of the inflation tube 44. Force is transferred through the inflation tube 44 to the main body 58 of the indwelling catheter 20. The pulling force constricts and elongates the coils of the coiled section 54, thereby reducing their transverse dimension as a result of longitudinally separating the individual coils with the pulling force. The reduced transverse dimension lessens or eliminates contact with the urinary canal 36. In this manner the coiled section 54 does not inhibit removal of the catheter or induce significant discomfort as it moves through the urinary canal. The amount of force transferred is sufficient to move the main body 58 of the indwelling catheter 20 past the external urinary sphincter muscle 34 and into the urinary canal 36. The deflated balloon 40 does not resist movement of the distal end of the indwelling catheter 20 through the bladder neck 46. Continued pulling movement on the inflation tube 44 moves the indwelling catheter 20 through the urinary canal 36 until the indwelling catheter 20 is completely withdrawn from the proximal end of the urinary canal 36. The control cord 57 can be pulled simultaneously with the pulling force on the inflation tube 44, as the indwelling catheter 20 is withdrawn from the urinary canal 36.

Figure 10:
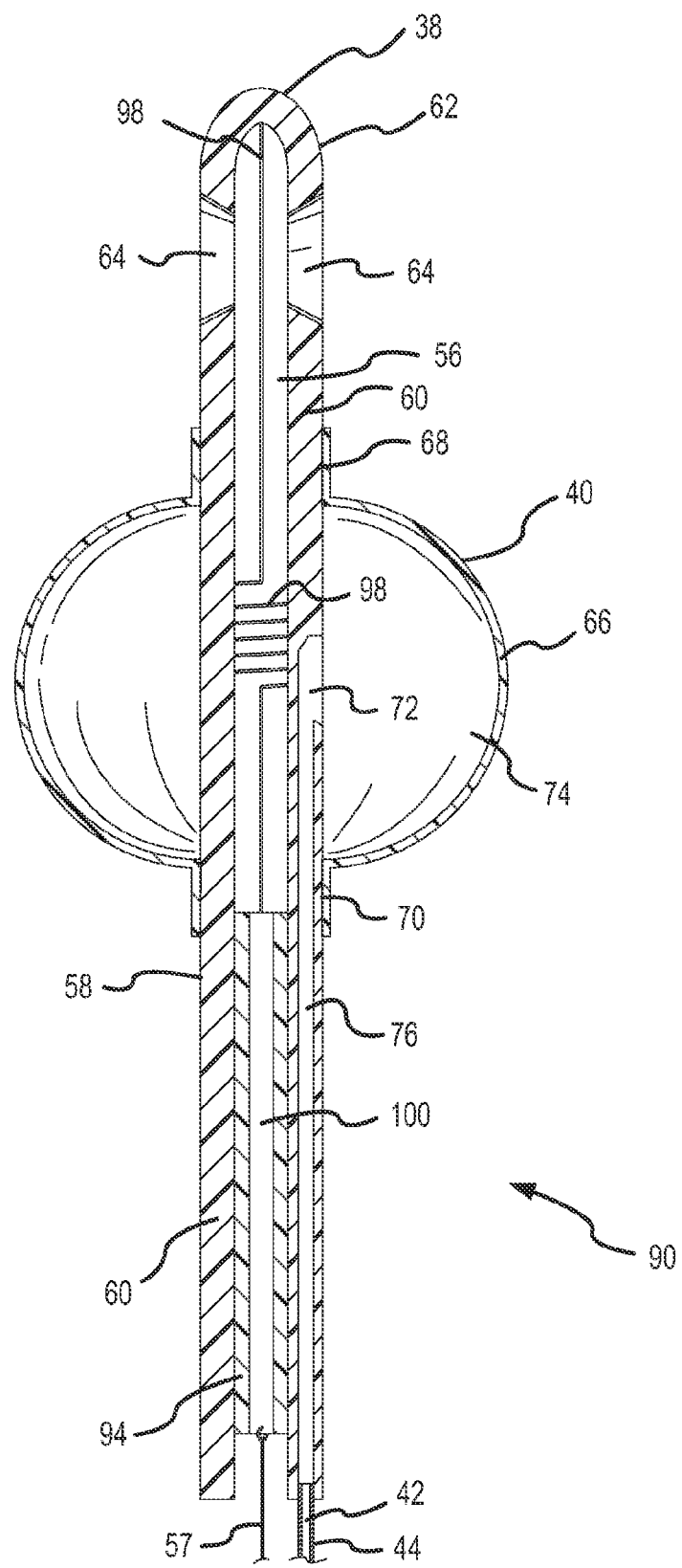
FIG. 10 is an enlarged longitudinal cross-section view of another form of a partial-length indwelling catheter of the present invention which uses a telescoping or extendable tube member.
Figure 11:
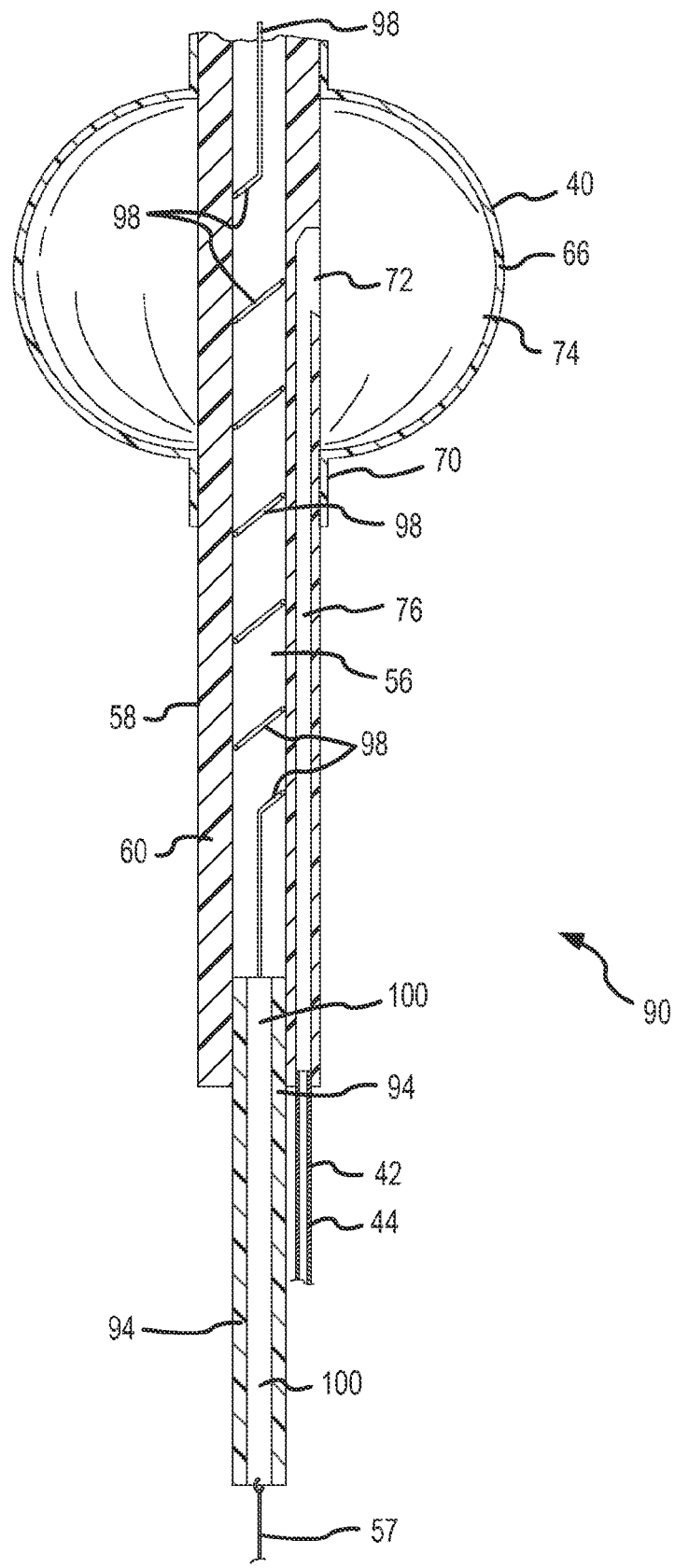
FIG. 11 is a partial view of the indwelling catheter shown in FIG. 10, showing the telescoping tube member in an extended position.
Figure 12:
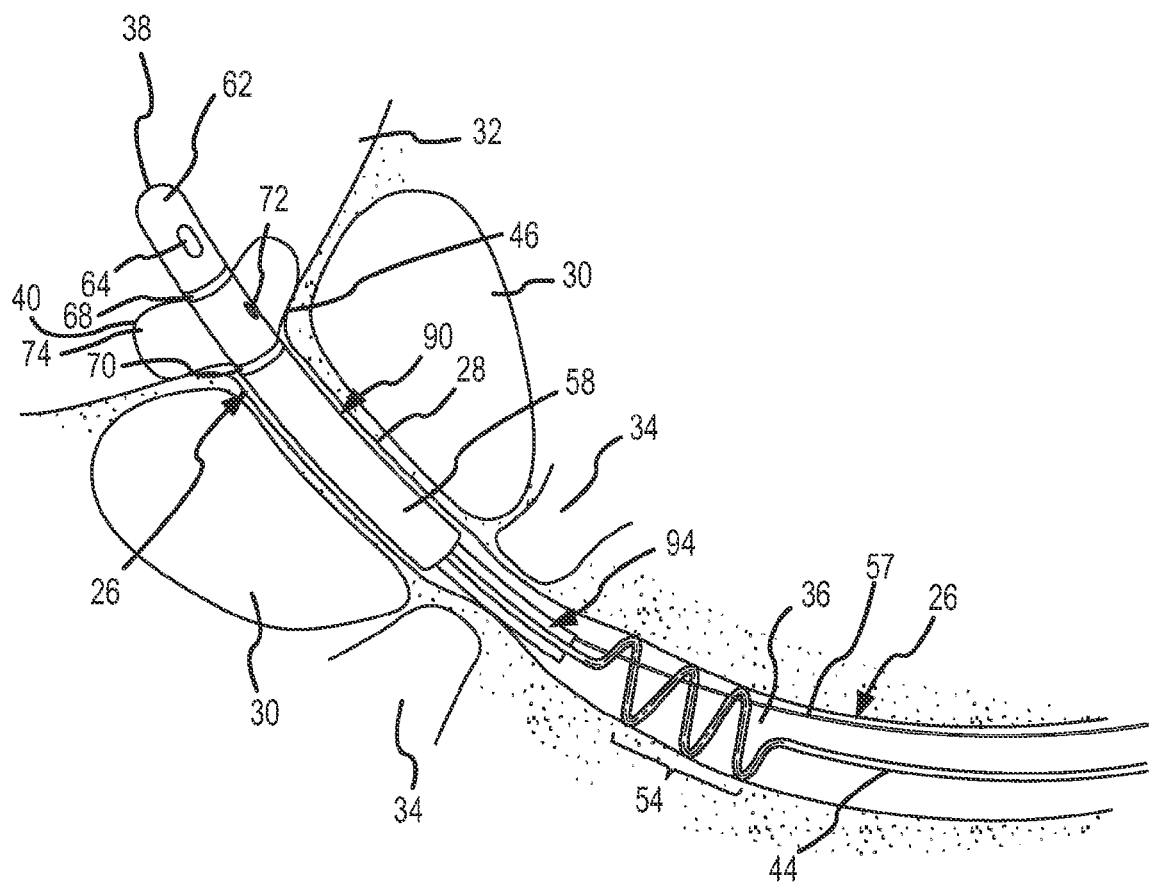
FIG. 12 is an illustration similar to FIG. 9, showing use of the indwelling catheter shown in FIGS. 10 and 11 when discharging urine through an orifice of the external urinary sphincter muscle.
Figure 13:
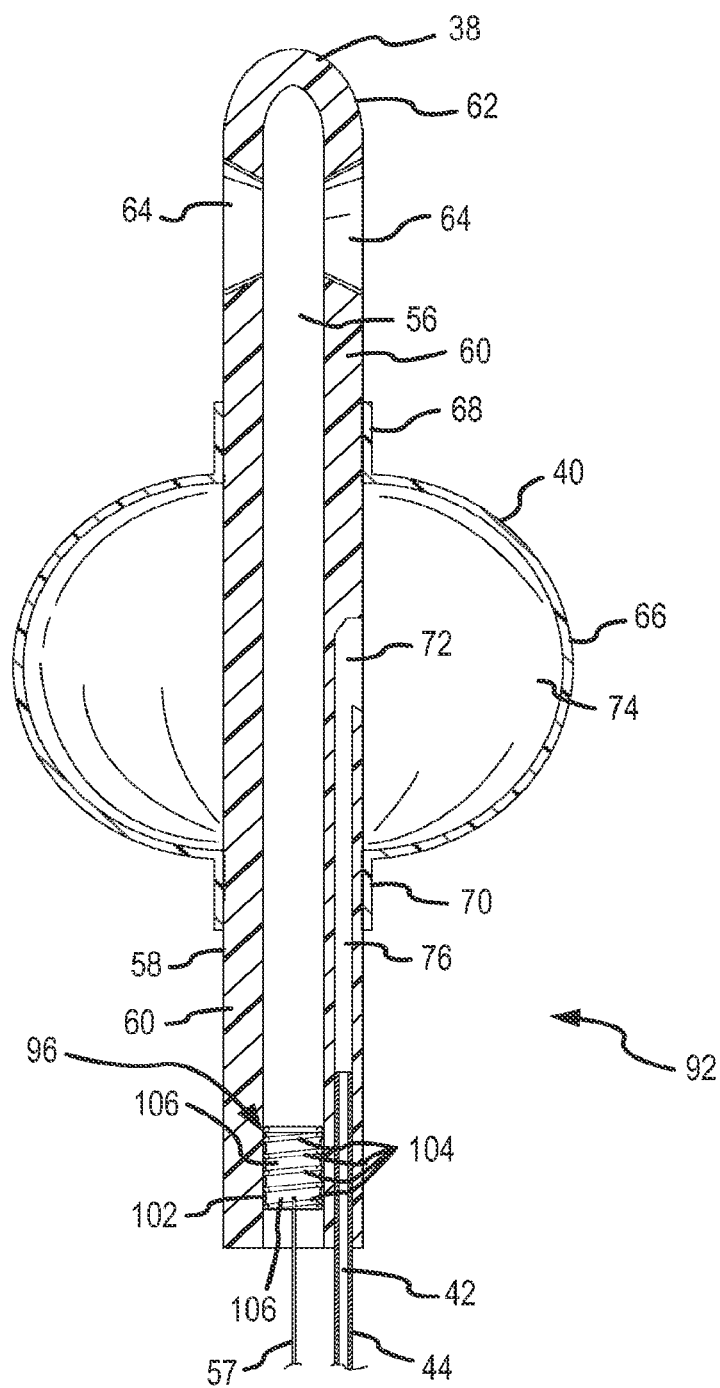
FIG. 13 is an enlarged longitudinal cross-section view of another form of a partial-length indwelling catheter of the present invention which uses an extendable and flexible sleeve member.
Figure 14:
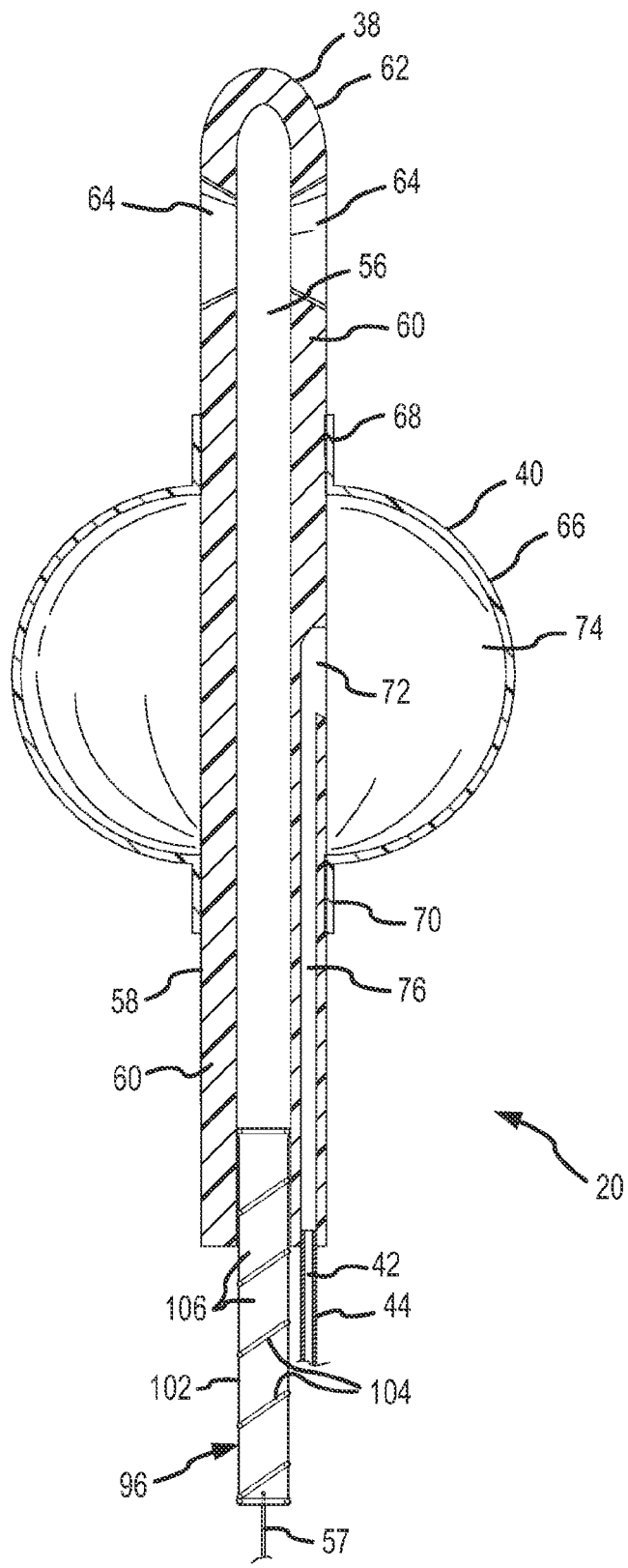
FIG. 14 is a partial view of the indwelling catheter shown in FIG. 13, showing the flexible sleeve member in an extended position.
Figure 15:
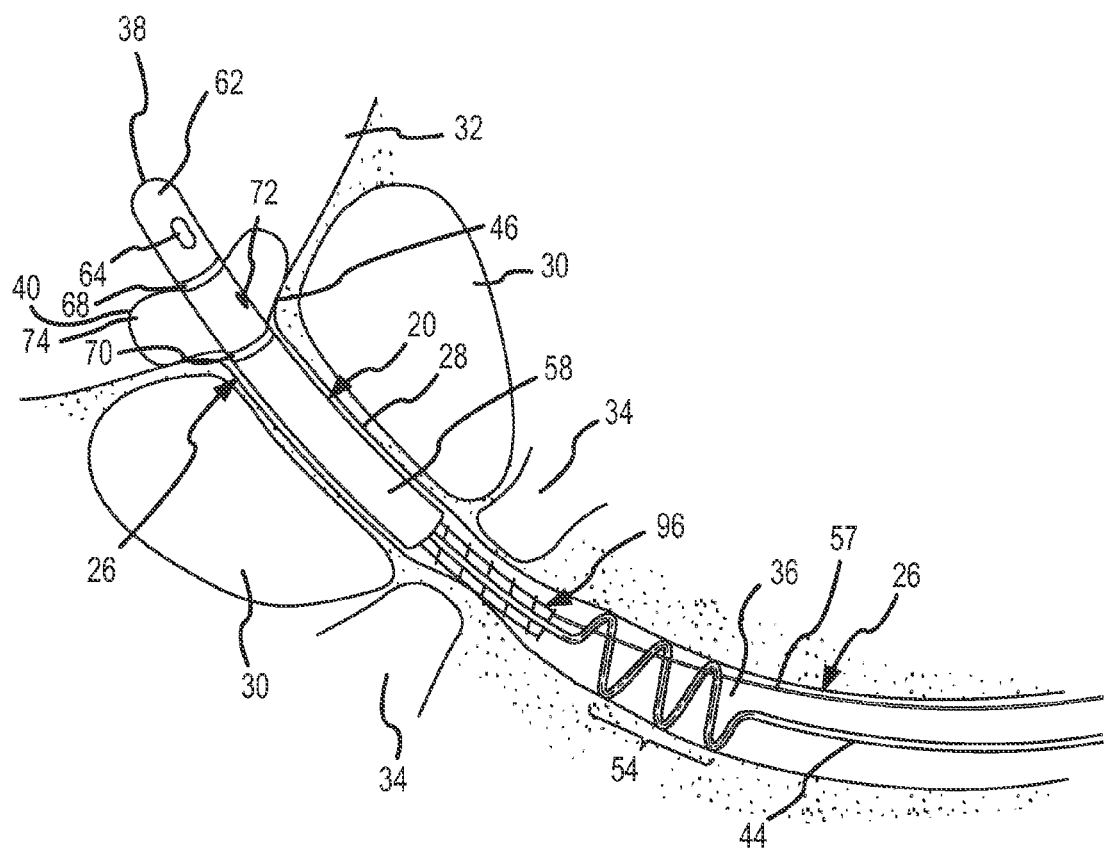
FIG. 15 is an illustration similar to FIGS. 9 and 12, showing use of the indwelling catheter shown in FIGS. 13 and 14 when discharging urine through an orifice of the external urinary sphincter muscle.

Alternative embodiments 90 and 92 of the indwelling catheter 20 are shown in FIGS. 10-12 and FIGS. 13-15 respectively. The indwelling catheter 90, shown in FIGS. 10-12, has a tube member 94 which is retained in a telescoping matter within the interior passageway 56 at the proximal end of the main body 58. The control cord 57 is attached to the proximal end of the tube member 94. Pulling force applied to the control cord 57 causes the telescoping tube member 94 to move from the proximal end of the main body 58, as shown in FIG. 11, and through the prostatic urethra slightly upstream or distal from the external urinary sphincter muscle 34, thereby opening the orifice and extending through the external urinary sphincter muscle 34, as shown in FIG. 12. The indwelling catheter 92, shown in FIGS. 13-15, uses an expandable and retractable sleeve member 96 which is retained within the interior passageway 56 at the proximal end of the main body 58. The control cord 57 is attached to the proximal end of the expendable and retractable sleeve member 96. Pulling force applied to the control cord 57 causes the sleeve member 96 to expand proximally outwardly in an accordion-like manner from the proximal end of the main body 58, as shown in FIG. 14, and extend through the prostatic urethra slightly upstream or distal from the external urinary sphincter muscle 34, thereby opening the orifice and extending through the external urinary sphincter muscle 34, as shown in FIG. 15.

The indwelling catheters 90 and 92 drain urine from the bladder 32, the interior passageway 56 within the main body 58, and through the telescoping tube member 94 or expandable sleeve member 96, respectively, into the urinary canal 36 past the sphincter muscle 34. Thereafter the urine flows through the urinary canal 36 and out of the exterior opening of the urinary tract at the penis, thereby effectively bypassing and overcoming the inability of a weak bladder to produce enough fluid pressure to dilate the external urinary sphincter muscle 34 naturally. After urination is complete, the telescoping tube member 94 and the expandable sleeve member 96 retract distally out of the urinary sphincter muscle 34 and back into the main body 58, thereby allowing the external urinary sphincter muscle 34 to close its orifice and prevent further unintended urine discharge.

In the indwelling catheters 90 and 92, the telescoping tube member 94 and the expandable and contractible flexible sleeve member 96 become urine conducting conduits which are selectively extendable from the main body 58. Pulling force on the control cord 57 extends the extendable urine conducting conduits 94 and 96, while the main bodies 58 of the indwelling catheters 90 and 92 remain essentially in a fixed or stable position within the prostatic urethra 28 and the bladder 32. The pulling force applied on the control cord 57 does not displace the main body 58 or compress the balloon 40, as is the case with the indwelling catheter 20. Consequently, there is no risk of compressing the balloon 40 an excessive amount which might lead to inadvertently rupturing the balloon 40 or to irritating the bladder neck 46 due to expansion or distention of it as a result of compressing the balloon 40 against and within it when the main body 58 of the indwelling catheter 20 is moved proximally as shown in FIG. 9. Instead, the pulling force on the control cord 57 moves the telescoping tube 94 or the expandable sleeve 96 through the short segment of the distal prostatic urethra 28 and through the orifice of the external urinary sphincter muscle 34, without the significant resistance and potential discomfort caused by moving the entire main body 58 of the indwelling catheter 20.

The use of the extendable urine conducting conduits 94 and 96 also allows the main bodies 58 of the catheters 90 and 92 to be a set or fixed size for different physiological lengths of the prostatic urethra 28 within different males. Despite the fixed length of the main body 58 within the prostatic urethra, the telescoping tube member 94 or the expandable sleeve member 96 may be extended a sufficient distance to open any proximal obstruction of the prostatic urethra and to open the orifice through the external sphincter muscle 34. A greater selective length of the entire urine drainage passageway through the indwelling catheter and into the urinary canal 36 is therefore made possible by the extendable members 94 and 96.

More details of the catheter 90 are explained in conjunction with FIGS. 10-12. The telescoping tube member 94 of the catheter 90 fits within the interior passageway 56 of the main body 58 and moves from a retracted position shown in FIG. 10 to an extended position shown in FIG. 11, by sliding longitudinally in the interior passageway 56. The telescoping tube member 94 is normally biased into the retracted position within the main body 58 by a retraction spring 98. The retraction spring 98 attaches at one end to the end piece 62 of the main body 58 within the interior passageway 56 and at the other end to the distal end of the tube member 94. In its normally retracted position within the interior passageway 56 (FIG. 10), no portion of the tube member 94 extends beyond the proximal end of the main body 58. The control cord 57 is attached to the proximal end of the tube member 94, such as tying it through a small opening formed through the side wall of the tube member 94. Pulling the control cord 57 with sufficient force to overcome the bias of the retraction spring 98 causes the tube member 94 to move proximally from the retracted position within the main body 58 into the extended position (FIG. 11). A restraint, such as a radial protrusion extending from the exterior surface of the tube member 94 into a slot formed in the interior sidewall surface of the main body 58 (none of which is shown), prevents the tube member 94 from moving completely out of the proximal end of the interior passageway 56.

With the catheter 20 inserted in the prostatic urethra 28, pulling the control cord 57 causes the tube member 94 to force open the orifice of the external urinary sphincter muscle 34, as shown in FIG. 12, as the tube member 94 moves into its extended position. In the extended position, an interior urine drainage lumen 100 of the tube member 94 conducts urine from the interior passageway 56 of the main body 58 through the external urinary sphincter muscle 34 and into the urinary canal 36 on the proximal side of the sphincter muscle 34. Once the urine is delivered to the downstream or proximal side of the external urinary sphincter muscle 34, the urine thereafter drains naturally through the remaining portion of the urinary canal and exits the penis where the urinary canal 36 opens to the exterior of the body.

After completing urination, the control cord 57 is released and the retraction spring 98 moves the tube member 94 from its extended position distally out of the orifice of the external urinary sphincter muscle 34 and back to the retracted position within the interior passageway 56 of the main body 58. The external urinary sphincter muscle 34 is then free to contract its orifice around the control cord 57 and the inflation tube 44 to prevent further urine flow, in a natural manner.

More details of the catheter 92 are explained in conjunction with FIGS. 13-15. The expandable and contractible flexible sleeve member 96 comprises a relatively thin wall 102 of flexible material, such as thin plastic, which is coated, molded or otherwise fitted around or integrally incorporated around a coil spring 104. The flexible wall 102 and the coil spring 104 are connected or integrated together in such a way to allow the coil spring 104 to be extended longitudinally while the wall 102 extends between each of the individual coils of the extended coil spring 104, as shown in FIG. 14. The wall 102 is sufficiently flexible and thin so that movement of the coil spring 104 from its extended position to a retracted position, shown in FIG. 13, is not significantly inhibited by the wall 102. The relatively thin and flexible wall 102 folds in an accordion-like manner between each of the individual coils of the spring 104, to allow the individual coils of the spring 104 to assume a position essentially compressed or adjacent to one another. Because it folds in the accordion-like manner, the flexible wall 102 does not inhibit the retraction of the coil spring 104. In both the extended and retracted positions of the expandable sleeve member 96, the wall 102 extends continuously and integrally along the length of the coil spring 104.

The expandable sleeve member 96 has an external dimension that is slightly smaller than the internal dimension of the interior passageway 56 of the main body 58, which allows the expandable sleeve member 96 to be positioned within the interior passageway 56. The distal end of the sleeve member 96, which includes the entire distal coil of the coil spring 104 and the wall 102 which surrounds that distal coil of the spring 104, is attached securely and stationarily to inside surface of the interior passageway 56, such as with an adhesive. Consequently, the distal end of the sleeve member 96 will not move relative to the main body 58. The remaining proximal portions of the expandable sleeve member 96, including the other coils of the coil spring 104 and the portions of the wall 102 which surround them, all of which are located proximally of the rigid attachment at the distal end, are free to move proximally within the interior passageway 56. Attaching the distal end of the expandable sleeve member 96 within the interior passageway 56 also creates an internal urine drainage lumen 106 through the sleeve member 96. The continuous integral wall 102 defines the urine drainage lumen 106 through the sleeve member 102.

The control cord 57 attaches to the proximal end of the expandable sleeve member 96. The attachment may occur as a result of looping and end of the control cord 57 around the proximal individual coil of the coil spring 104 by forming a small hole through the wall 102. The end of the control cord 57 is tied to the individual coil, thereby securely attaching the control cord to the proximal end of the expandable sleeve member 96. Pulling the control cord 57 causes the sleeve member 96 to expand longitudinally within the interior passageway 56 until a proximal end of the sleeve member 96 extends from the main body 58. The sleeve member 96 expands from the main body 58 to an extended position to open the orifice through the external urinary sphincter muscle 34, as shown in FIG. 15. The internal urine drainage lumen 106 continues a fluid conduction path from the interior passageway 56 of the main body 58 through the length of the expandable sleeve member 102. Urine is able to flow from the bladder 32 through the interior passageway 56 and through the internal urine drainage lumen 106 into the urinary canal 36 on the downstream or proximal side of the external urinary sphincter muscle 34. Once the urine is delivered to the downstream or proximal side of the external urinary sphincter muscle 34, the urine thereafter drains naturally through the remaining portion of the urinary canal and exits the penis where the urinary canal 36 opens to the exterior of the body.

When urination is completed, the control cord 57 is released and the internal coil spring 104 retracts the expandable sleeve member 96 out of the orifice through the sphincter muscle 34 and back into the interior passageway 56 of the main body 58. After the expandable sleeve member 96 is retracted from the external sphincter muscle 34, the muscle 34 contracts to close the orifice around the inflation tube 44 and the control cord 57 to stop urine flow from the bladder 32 in a natural manner.

The indwelling catheters 90 and 92, shown in FIGS. 10-15, are inserted into the urinary tract 26 in essentially the same manner as the catheter 20 is inserted, as has been previously described. The telescoping tube member 94 and the expandable sleeve member 96, when in their retracted positions shown in FIGS. 10 and 13, respectively, provide a sufficient space at the proximal end of the main body 58 to permit the sleeve 84 on the distal end of the insertion tool 22 to mate with the main body 58 to create the separable connection 52 for inserting the indwelling catheter 20, as shown in FIG. 5. Consequently, the insertion tool 22 can be connected to the catheters 90 and 92 in the same manner as it is connected to the catheter 20, to permit the catheters 90 and 92 to be inserted in the manner previously described.

Although the coil 54 of the inflation tube 44 (FIGS. 2, 3, 6-9, 15 and 16) functions effectively as a proximal anchor for the catheter 20, 90 and 92 in the manner described, under some circumstances the coil 54 may prove unnecessary. The extension of the inflation tube 44 through the urinary canal 36 creates some restriction or resistance against distal movement of the catheter from its normal position, and that resistance is enhanced by the normal constriction of the external urinary sphincter muscle 34 around the inflation tube 44 except during urine discharge. Some distal movement of the catheter from its normal position may be tolerated, because the control cord 57 can be pulled to return the catheter to the normal position with the balloon 40 in contact with the bladder neck 46. Moving the catheter from a distally-displaced position back to the normal position is also facilitated by pulling on the inflation tube 44 simultaneously while pulling on the control cord 57, apart from whether the coil 54 is included in the inflation tube 44.

Under certain circumstances, blood clots or other obstructions may form in the bladder 32 and obstruct the fluid flow openings 64 from the bladder into the interior passageway 56. To eliminate those clots or other obstructions, it may become necessary or desirable to flush the interior passageway 56 with saline or another appropriate flushing liquid on a periodic basis. The flushing fluid may be delivered to the catheters 20, 90 and 92 through the interior channel 88 of the insertion tool 22 while the insertion tool remains connected to the indwelling catheter, after insertion of the indwelling catheter. Flushing the indwelling catheter is described in greater detail in the previous U.S. patent application noted above of which this invention is a continuation in part. In general, however, the flushing fluid is forced from the handle 82 through the interior channel 88 of the insertion tool 22, through the center opening 86 of the sleeve 84 and into the interior passageway 56. The flushing fluid dissolves any clots within the interior passageway 56 or openings 64, and keeps the passageway 56 unobstructed for urine flow from the bladder 32. The dissolved clots flow from the interior passageway 56 through the interior channel 88 and out the urinary canal 36, or the clots are pushed back into the bladder 32 with the flushing fluid where they may dissolve in the urine within the bladder.

A fluid communication path for flushing the indwelling catheters 20, 90 and 92 may be established after the insertion tool 22 has been disconnected and separated from the indwelling catheter 20. The control cord 57 is used as a guide for directing the insertion tool 22 back through the urinary canal 36 until it contacts the indwelling catheter and reestablishes the separable connection 52 (FIG. 5). The insertion tool 22 is inserted over the proximal end of the control cord 57 and is pushed distally into the urinary canal 36 while the control cord 57 is held taunt enough to establish a guide for the insertion tool 22 as it moves into the urinary canal. The insertion tool 22 follows the cord 57 through the center of the coiled section 54 of the inflation tube 44 to the orifice of the external urinary sphincter muscle 34. Continued distal movement of the insertion tool 22 forces the orifice of the sphincter muscle 34 open and allows the insertion tool 22 to pass through. The distal movement of the insertion tool 22 is then continued until the sleeve 84 of the insertion tool 22 enters into the proximal end of the interior passageway 56 to reestablish the separable connection 52 shown in FIG. 5. In the catheters 90 and 92, the slight tension force in the control cord 59 is relaxed so that the telescoping tube member 94 or the expandable sleeve member 96 retracts into the main body 58 of the catheter, thereby allowing the sleeve 84 to enter the interior passageway 56 and reestablish the separable connection 52. Flushing fluid is then directed through the insertion tool 22 into the interior passageway 56 to remove obstructions from within the interior passageway 56.

Alternatively, the proximal end of the indwelling catheter 20 may be moved through the orifice of the external urinary sphincter muscle 34 by pulling the control cord 57, and while in this position the separable connection 52 with the insertion tool 22 is reestablished while the proximal end of the main body 58 is located proximally or downstream of the orifice in the external urinary sphincter muscle 34. As a further alternative, a flushing tube 108, shown in FIG. 16, may be used instead of the insertion tool 22. The distal end of the flushing tube 108 may have a size comparable to the sleeve 84, thereby allowing it to be inserted into the proximal end of the main body 58 in essentially the same manner that the sleeve 84 of the insertion tool 22 is inserted (not shown in FIG. 16). The flushing tube 108 includes an interior channel or passageway through which the flushing fluid is forced into the interior passageway 56 of the catheters 20, 90 and 92 to flush away any obstructions.

Figure 16:
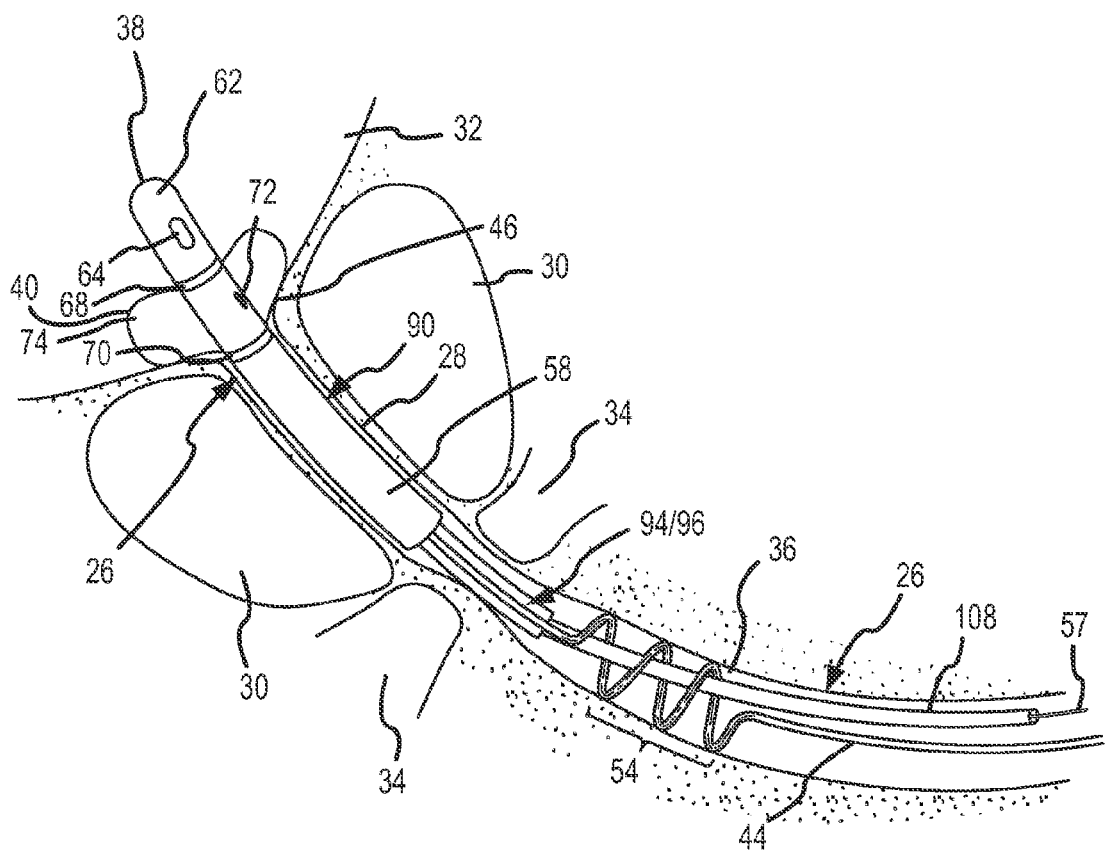
FIG. 16 is an illustration similar to FIGS. 12 and 15, additionally showing the use of a flushing tube with the indwelling catheters shown in FIGS. 10 and 13.

Establishing a flushing fluid communication path with the telescoping tube member 94 of the catheter 90 or the expandable sleeve member 96 of the catheter 92 can also be accomplished by using the flushing tube 108, as shown in FIG. 16. The control cord 57 is pulled to move the tube member 94 or the sleeve member 96 proximally into and through the orifice of the external urinary sphincter muscle 34. The control cord 57 is threaded through the interior channel of the flushing tube 108, and the flushing tube 108 is inserted and moved distally through the urinary canal 36 while following the control cord 57 until the flushing tube 108 contacts the proximal end of either the tube member 94 or the sleeve member 96. The exterior size or diameter of the flushing tube 108 is sized to fit into the interior urine drainage lumen 100 or 106 of the tube member 94 or the sleeve member 96, respectively. Thereafter, flushing fluid is delivered through the interior channel or passageway of the flushing tube 108. The flushing fluid passes through the lumen 100 or 106 into the interior passageway 56 to flush, dissolve, remove or displace the clots or obstructions. The fluid communication path from the flushing tube 108 into the tube member 94 or the sleeve member 96 need not be fluid tight for the flushing fluid to remove the obstructions, if sufficient fluid flow and pressure from the flushing fluid are available.

Although the flushing tube 108 shown in FIG. 16 is of a size which fits within the interior urine drainage lumen 100 or 106 of the telescoping tube member 94 or the expandable sleeve member 96, the flushing tube 108 could be made of a larger size to allow its interior channel or passageway to fit over the tube member 94 or the sleeve member 96. Under such circumstances, the tube member 94 or the sleeve member 96 should be moved into the extended position, so that the fluid connection is established between the larger sized flushing tube 108 and the extended tube member 94 or sleeve member 96 on the proximal or downstream side of the external urinary sphincter muscle 34. With a flushing tube 108 of a relatively smaller diameter, it is possible to establish the fluid connection with the indwelling catheter 90 or 92 while its tube member 94 or sleeve member 96 is in the retracted position. Under these circumstances, the smaller diameter flushing tube 108 is moved distally through the orifice of the external urinary sphincter muscle and into the interior urine drainage lumen 100 or 106 while the tube member 94 or sleeve member 96 is in the retracted position. Under these circumstances, the coiled section 54 of the inflation tube 44 serves as an anchor to prevent forcing the catheter 90 or 92 into the bladder 32.

In addition to its beneficial use in avoiding the need to use a full-length catheter, the partial-length indwelling catheters 20, 90 and 92 are also useful in diagnosing urinary retention problems caused by a weak bladder or a prostatic urethra blockage. Both a weak bladder or a prostatic urethra blockage may cause reduced (or in severe cases terminated) urinary flow, but the treatment of prostatic urethra blockage differs substantially from the treatment of a weak bladder. Therefore, it is very important to correctly diagnose the cause of this type of urinary tract retention. In addition to diagnosing a weak bladder or a prostatic urethra blockage, the partial-length indwelling catheter may also be useful in implicating certain types of neurogenic disorders to the external urinary sphincter muscle.

Figure 17:
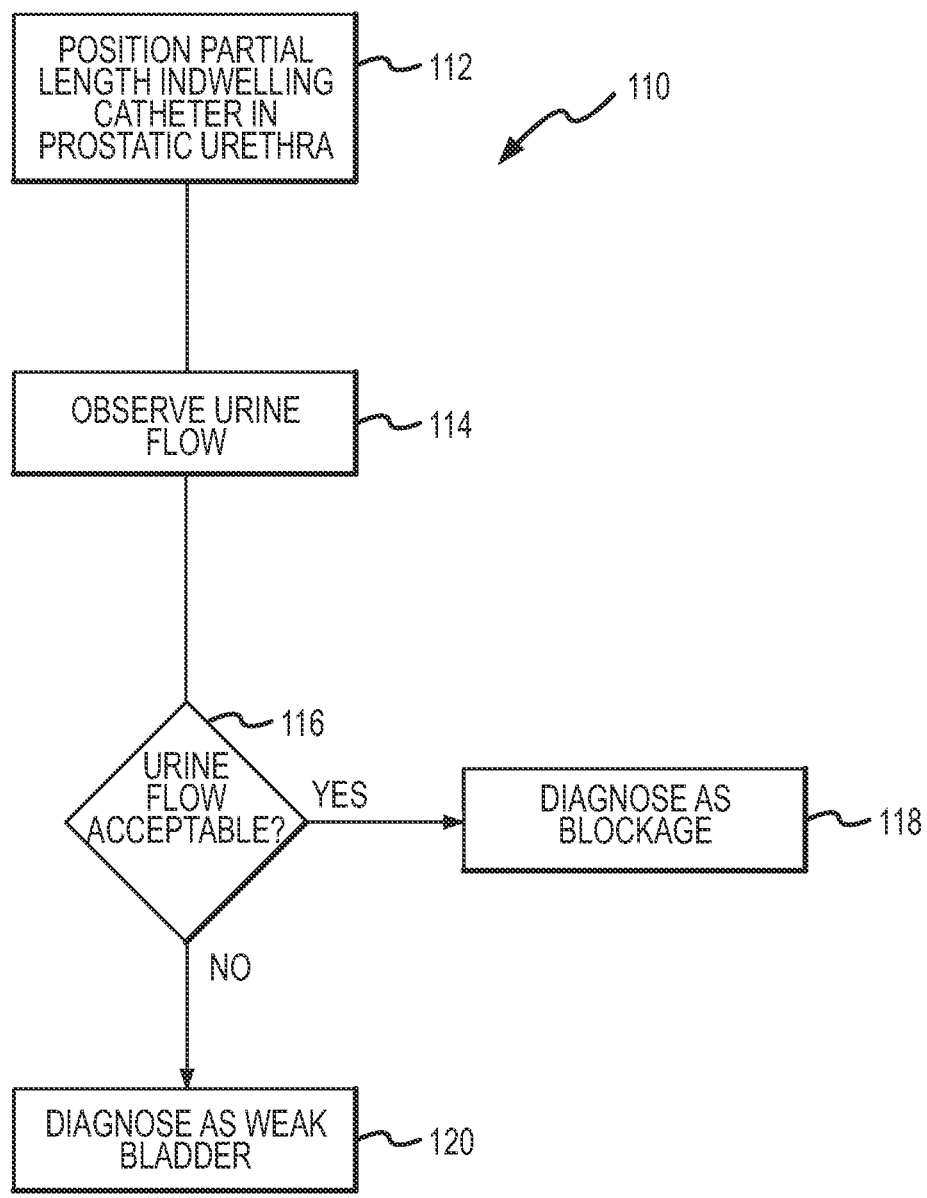
FIG. 17 is a flow chart showing the use of a partial-length indwelling catheter for diagnosing a prostatic urethra obstruction or a weak bladder condition.

The typical procedure for diagnosing a weak bladder involves a cystometry study. A cystometry study is uncomfortable, time-consuming, expensive and may increase the risk of a urinary infection. A partial-length indwelling catheter, such as the catheters 20, 90 and 92 or the catheters described in the aforementioned previously-filed U.S. patent applications, can be used in an effective and reliable method to diagnose a weak bladder or prostatic urethra blockage in a straightforward manner without significant expense, time consumption, discomfort or increased risk of a urinary infection. A method 110 of diagnosing a weak bladder or a prostatic urethra blockage by using such a partial-length indwelling catheter is shown in FIG. 17. As shown in FIG. 17, each of the steps of the method 110 is indicated by a separate reference number.

The method 110 commences by inserting the partial-length indwelling catheter into the urinary canal 36 until the catheter is in its use position (e.g. FIG. 8), as shown at 112. After the indwelling catheter 20 is inserted, the flow of urine is observed at 114. Next, at 116, a determination is made as to whether the urine flow is normal or acceptable on one hand, or whether the urine flow is less than acceptable on the other hand. If the urine flow is acceptable, the cause of the reduced urinary flow is a prostatic urethra blockage as indicated at 118. An acceptable urine flow results because the positioning of the partial-length catheter within the prostatic urethra will have created an unrestricted interior passageway 56 of the catheter through which the urine from the bladder will flow. In other words, the presence of the partial-length catheter within the prostatic urethra opens a urine passageway despite the blockage created by the enlargement or swelling of the prostate gland. The acceptable level of urine flow through the indwelling catheter after the partial-length catheter has been inserted indicates that the unacceptable level of urine flow before the partial length indwelling catheter was inserted was caused by a prostatic urethra blockage, which is diagnosed at 118.

The open interior passageway 56 through the positioned partial-length catheter assures that the fluid pressure created by the bladder is communicated through the prostatic urethra to the external urinary sphincter muscle 34. Under these circumstances with a fluid pressure communication path established from the bladder through the catheter to the external urinary sphincter muscle 34, a weak bladder is implicated as the cause of inadequate urine flow if the orifice through the sphincter muscle 34 does not dilate and conduct an adequate urine flow. Therefore, if the determination at 116 indicates that the urine flow is still not acceptable, a weak bladder is indicated and diagnosed at 120.

The diagnosis at 120 is verified by either moving the main body 58 of the catheter 20, or the telescoping tube member 94 of the catheter 90, or the expandable sleeve member 96 of the catheter 92, to open the orifice through the external urinary sphincter muscle 34 and then observing the urine flow. If the level of urine flow is then acceptable, the weak bladder diagnosis at 120 is verified since the necessity to open the orifice through the external urinary sphincter muscle 34 indicates an inadequate pressure stimulus from the bladder to cause the external urinary sphincter muscle 34 to open naturally.

While a partial-length indwelling catheter which has no capability of mechanically opening the orifice through the external urinary sphincter muscle, such as those described in the aforementioned U.S. patent applications, may be effective in diagnosing a weak bladder by performing the method 110, the catheters 20, 90 and 92 are particularly useful in verifying the diagnosis of a weak bladder because of their capability of mechanically opening the orifice through the external urinary sphincter muscle to verify a weak bladder diagnosis.

The method described in FIG. 17 is also useful in diagnosing or implicating certain neurogenic disorders affecting the external urinary sphincter muscle. With the partial-length indwelling catheter inserted, any unintended urine discharge implicates a neurogenic disorder of the external urinary sphincter muscle because the orifice through that muscle is opened when it should be closed. On the other hand, with the partial-length indwelling catheter inserted, an inability to obtain urine discharge may implicate a neurogenic disorder of the external urinary sphincter muscle because the orifice through that muscle cannot be opened when desired. Thus, method of the present invention may be used to diagnose neurogenic disorders when a weak bladder or a prostatic urethra blockage has been ruled out. Alternatively, under conditions were neurogenic disorders have been ruled out, the method of the present invention is useful for diagnosing a prostatic urethra blockage or a weak bladder.

The method 110 described in connection with FIG. 17 is not effective to distinguish between a blockage between the proximal end of the main body 58 of the catheter 20, 90 or 92 and the distal side of the external urinary sphincter muscle 34. In general, a blockage in this relatively short segment of the prostatic urethra does not occur as a result of prostate gland disease, because the blockage is more widespread and located more centrally within the prostatic urethra. A blockage in this relatively short segment does sometimes arise as a result of tissue swelling after treatments involving a transurethral resection of the prostate (TURP), transurethral microwave thermotherapy (TUMT), radio frequency needle ablation (TUNA), interstitial laser and hot water induced thermotherapy (WIT). Because the swelling is predictable after these types of treatments, there is usually not a concern about correctly distinguishing between a weak bladder condition and a prostatic urethra obstruction. Consequently, the effectiveness of the method 110 remains very useful and productive in diagnosing urinary retention problems caused by a prostatic obstruction or a weak bladder.

The partial-length catheters 20, 90 and 92 allow the voluntary and natural use of the external urinary sphincter muscle 34 to start and stop urine flow. The location of the indwelling catheter within the prostate gland 30 bypasses most of the urine flow from contact with the tissue of the prostate gland 30 which has been affected by the surgical procedure, thereby preventing or lessening pain and irritation. The catheters 20, 90 and 92 also assure a passageway for urine to flow through a prostate gland which is diseased or swollen from BPH or other diseases or from surgical treatment. Males with a weak bladder benefit from using the indwelling catheters 20, 90 or 92 because of the selective ability to control urine discharge without using a full-length catheter. Many other benefits and advantages have been described above or will become apparent upon appreciating the full ramifications of the present invention.

Presently preferred embodiments of the invention and many of its improvements have been described above with a degree of particularity. The description is of preferred examples for implementing the invention, and is not necessarily intended to limit the scope of the invention. The scope of the invention is defined by the following claims.

What is claimed:

1. A partial-length indwelling catheter for draining urine in a male human from the bladder through the urethal opening of the bladder which is surrounded by the bladder neck and into the prostatic urethra within the prostate gland and through the orifice in the external urinary sphincter muscle and into the urinary canal which ends at the exterior opening of the urinary canal, the urine flowing from a distal location at the bladder to a proximal location at the exterior opening, the catheter comprising:

a main body having a distal end and a proximal end, the main body having a length sufficient to establish a normal position in which the distal end is within the bladder and the proximal end is distally adjacent to the external urinary sphincter muscle, the main body defining an interior passageway extending from the distal end to the proximal end, the interior passageway communicating with the urine within the bladder;

an inflatable balloon attached on the distal end of the main body, the inflatable balloon contacting the bladder neck and restraining the main body against proximal movement from the normal position when the inflatable balloon is inflated within the bladder;

an inflation tube having a distal end connected to the main body and a length sufficient to extend from the main body through the orifice in the external urinary sphincter muscle and the urinary canal to the exterior opening at which a proximal end of the inflation tube is located, the inflation tube and the main body defining an inflation passageway extending from the proximal end of the inflation tube in communication with the inflatable balloon through which to deliver fluid for inflating the balloon; and a control element having a distal end connected to the main body and having a length sufficient to extend through the orifice of the external urinary sphincter muscle and through the urinary canal to a proximal end located outside the exterior opening when the main body is in the normal position, the control element transferring force from the proximal end of the control element to the main body to selectively displace the proximal end of the main body in a proximal direction from the normal position through the orifice of the external urinary sphincter muscle to conduct urine from the bladder through the interior passageway and into the urinary canal at a position proximal of the external urinary sphincter muscle.

2. An indwelling catheter as defined in claim 1, wherein:
the control element transfers sufficient force to move the main body in the proximal direction relative to the normal position to selectively displace the proximal end of the catheter in a proximal direction from the normal position through the orifice in the external urinary sphincter muscle.

3. An indwelling catheter as defined in claim 2, wherein:
the control element comprises a control cord connected to the main body; and
the control cord transfers pulling force which is sufficient to compress the inflatable balloon against the bladder neck and move the main body in the proximal direction to thereby displace the proximal end of the main body from the normal position in a proximal direction through the orifice of the external urinary sphincter muscle.

4. An indwelling catheter as defined in claim 3, wherein:
the force of compressing the inflatable balloon against the bladder neck to displace the proximal end of the main body in the distal direction through the orifice of the external urinary sphincter muscle returns the main body to the normal position after releasing the pulling force on the control cord.

5. A partial-length indwelling catheter for draining urine in a male human from the bladder through the urethal opening of the bladder which is surrounded by the bladder neck and into the prostatic urethra within the prostate gland and through the orifice in the external urinary sphincter muscle and into the urinary canal which ends at the exterior opening of the urinary canal, the urine flowing from a distal location at the bladder to a proximal location at the exterior opening, the catheter comprising:

a main body having a distal end and a proximal end, the main body having a length sufficient to establish a normal position in which the distal end is within the bladder and the proximal end is distally adjacent to the external urinary sphincter muscle, the main body defining an interior passageway extending from the distal end to the proximal end, the interior passageway communicating with the urine within the bladder;

an inflatable balloon attached on the distal end of the main body, the inflatable balloon contacting the bladder neck and restraining the main body against proximal movement from the normal position when the inflatable balloon is inflated within the bladder;

an inflation tube having a distal end connected to the main body and a length sufficient to extend from the main body through the orifice in the external urinary sphincter muscle and the urinary canal to the exterior opening at which a proximal end of the inflation tube is located, the inflation tube and the main body defining an inflation passageway extending from the proximal end of the inflation tube in communication with the inflatable balloon through which to deliver fluid for inflating the balloon; and a control element having a distal end connected to the main body and having a length sufficient to extend through the orifice of the external urinary sphincter muscle and through the urinary canal to a proximal end located outside the exterior opening when the main body is in the normal position, the control element transferring force from the proximal end of the control element to the main body to selectively displace the proximal end of the main body in a proximal direction from the normal position through the orifice of the external urinary sphincter muscle to conduct urine from the bladder through the interior passageway and into the urinary canal at a position proximal of the external urinary sphincter muscle, and wherein:

the main body includes an extendable proximal end portion which is extendable in a proximal direction relative to the main body to effectively extend the length of the main body and the interior passageway of the main body; and the control element is connected to the extendable proximal end portion of the main body to move the extendable proximal end portion in a proximal direction relative to the normal position through the orifice of the external urinary sphincter muscle when the main body is in the normal position with the inflated balloon contacting the bladder neck.

6. An indwelling catheter as defined in claim 5, further comprising:
a bias element connected between the extendable proximal end portion and the main body to return the extendable proximal end portion from extending through the orifice of the external urinary sphincter muscle to a position distal of the orifice of the external urinary sphincter muscle upon ceasing application of force on the control cord.

7. An indwelling catheter as defined in claim 5, wherein:
the extendable proximal end portion of the main body comprises a tube member which is telescopically movable relative to the main body.

8. An indwelling catheter as defined in claim 7, wherein:
the control element comprises a control cord connected to the telescoping tube member; and
the control cord transfers pulling force which is sufficient to move the telescoping tube member in the proximal direction relative to the main body and through the orifice of the external urinary sphincter muscle.

9. An indwelling catheter as defined in claim 8, further comprising:
a bias element connected between the tube member and the main body to return the tube member from extending through the orifice of the external urinary sphincter muscle to a position distal of the orifice of the external urinary sphincter muscle upon ceasing application of pulling force on the control cord.

10. An indwelling catheter as defined in claim 5, wherein:
the extendable proximal end portion of the main body comprises a flexible sleeve member which is expandable relative to the main body.

11. An indwelling catheter as defined in claim 10, wherein:
the control element comprises a control cord connected to the flexible sleeve member; and
the control cord transfers pulling force which is sufficient to expand the flexible sleeve member in the proximal direction relative to the main body and through the orifice of the external urinary sphincter muscle.

12. An indwelling catheter as defined in claim 11, wherein:
the flexible sleeve member expands by flexing in an accordion-like manner.

13. An indwelling catheter as defined in claim 11, wherein:
the flexible sleeve member includes a bias element to retract the flexible sleeve member from extending through the orifice of the external urinary sphincter muscle upon ceasing application of pulling force on the control cord.

14. An indwelling catheter as defined in claim 5, wherein:
the extendable proximal end portion is movable to a retracted position in which the extendable proximal end portion is positioned entirely within the interior passageway of the main body.

15. A partial-length indwelling catheter for draining urine in a male human from the bladder through the urethal opening of the bladder which is surrounded by the bladder neck and into the prostatic urethra within the prostate gland and through the orifice in the external urinary sphincter muscle and into the urinary canal which ends at the exterior opening of the urinary canal, the urine flowing from a distal location at the bladder to a proximal location at the exterior opening, the catheter comprising:
  a main body having a distal end and a proximal end, the main body having a length sufficient to establish a normal position in which the distal end is within the bladder and the proximal end is distally adjacent to the external urinary sphincter muscle, the main body defining an interior passageway extending from the distal end to the proximal end, the interior passageway communicating with the urine within the bladder;
  an inflatable balloon attached on the distal end of the main body, the inflatable balloon contacting the bladder neck and restraining the main body against proximal movement from the normal position when the inflatable balloon is inflated within the bladder;
  an inflation tube having a distal end connected to the main body and a length sufficient to extend from the main body through the orifice in the external urinary sphincter muscle and the urinary canal to the exterior opening at which a proximal end of the inflation tube is located, the inflation tube and the main body defining an inflation passageway extending from the proximal end of the inflation tube in communication with the inflatable balloon through which to deliver fluid for inflating the balloon;
  a proximal anchor element connected to the main body and located at a position on the proximal side of the external urinary sphincter muscle when the inflatable balloon contacts the bladder neck, the proximal anchor element restraining the main body against distal movement from the normal position, the proximal anchor element comprising a coiled section of the inflation tube within the urinary canal located at a position proximal of the external urinary sphincter muscle; and
  a control element having a distal end connected to the main body and having a length sufficient to extend through the orifice of the external urinary sphincter muscle and through the urinary canal to a proximal end located outside the exterior opening when the main body is in the normal position, the control element transferring force from the proximal end of the control element to the main body to selectively displace the proximal end of the main body in a proximal direction from the normal position through the orifice of the external urinary sphincter muscle to conduct urine from the bladder through the interior passageway and into the urinary canal at a position proximal of the external urinary sphincter muscle.

16. An indwelling catheter as defined in claim 15, wherein:
the control element transfers sufficient force to move the main body in the proximal direction relative to the normal position to selectively displace the proximal end of the catheter in a proximal direction from the normal position through the orifice in the external urinary sphincter muscle.

17. An indwelling catheter as defined in claim 16, wherein:
the control element comprises a control cord connected to the main body; and
the control cord transfers pulling force which is sufficient to compress the inflatable balloon against the bladder neck and move the main body in the proximal direction to thereby displace the proximal end of the main body from the normal position in a proximal direction through the orifice of the external urinary sphincter muscle.

18. An indwelling catheter as defined in claim 17, wherein:
the force of compressing the inflatable balloon against the bladder neck to displace the proximal end of the main body in the distal direction through the orifice of the external urinary sphincter muscle returns the main body to the normal position after releasing the pulling force on the control cord.

* * * * *